US010927192B2

(12) United States Patent
Swadeshmukul et al.

(10) Patent No.: US 10,927,192 B2
(45) Date of Patent: *Feb. 23, 2021

(54) COMPOSITION AND METHOD OF MAKING WATER SOLUBLE CHITOSAN POLYMER AND COMPOSITE PARTICLES

(71) Applicant: University of Central Florida Research Foundation, Inc., Orlando, FL (US)

(72) Inventors: Santra Swadeshmukul, Orlando, FL (US); Basumallick Srijita, Orlando, FL (US)

(73) Assignee: University of Central Florida Research Foundation, Inc., Orlando, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 14/709,674

(22) Filed: May 12, 2015

(65) Prior Publication Data

US 2015/0327553 A1 Nov. 19, 2015

Related U.S. Application Data

(60) Provisional application No. 61/992,510, filed on May 13, 2014.

(51) Int. Cl.
| | |
|---|---|
| C08B 37/08 | (2006.01) |
| A01N 55/02 | (2006.01) |
| A01N 59/20 | (2006.01) |
| A61K 47/36 | (2006.01) |
| A61K 9/51 | (2006.01) |
| A61L 26/00 | (2006.01) |
| A61L 15/28 | (2006.01) |
| A61L 15/46 | (2006.01) |
| A61L 31/04 | (2006.01) |
| A61L 27/20 | (2006.01) |
| A61L 27/54 | (2006.01) |
| A61L 31/16 | (2006.01) |
| A61L 27/16 | (2006.01) |
| A61L 15/24 | (2006.01) |

(52) U.S. Cl.
CPC ........... *C08B 37/003* (2013.01); *A01N 55/02* (2013.01); *A01N 59/20* (2013.01); *A61K 9/5161* (2013.01); *A61K 9/5192* (2013.01); *A61K 47/36* (2013.01); *A61L 15/24* (2013.01); *A61L 15/28* (2013.01); *A61L 15/46* (2013.01); *A61L 26/0014* (2013.01); *A61L 26/0023* (2013.01); *A61L 26/0066* (2013.01); *A61L 27/16* (2013.01); *A61L 27/20* (2013.01); *A61L 27/54* (2013.01); *A61L 31/042* (2013.01); *A61L 31/048* (2013.01); *A61L 31/16* (2013.01)

(58) Field of Classification Search
CPC ...... A01N 59/20; A01N 55/102; A01N 25/10; A61L 27/20; A61L 27/16; A61L 27/54; A61L 26/0066; A61L 26/0014; A61L 26/0023; A61L 15/46; A61L 15/28; A61L 15/24; A61L 31/16; A61L 31/08; A61L 31/042; A61L 47/36; C08B 37/003; C08L 5/08; A61K 47/36; A61K 9/5161
USPC .......................................................... 536/20
See application file for complete search history.

(56) References Cited

U.S. PATENT DOCUMENTS

| | | | |
|---|---|---|---|
| 9,247,734 | B2 | 2/2016 | Sabin |
| 9,717,251 | B2 | 8/2017 | Sabin |
| 9,718,739 | B2 | 8/2017 | Sabin |
| 2011/0021745 | A1* | 1/2011 | Santra .................. A61K 9/5161 530/322 |

FOREIGN PATENT DOCUMENTS

WO   WO 2009/009469 A1 *   1/2009   ............. A61B 5/055

OTHER PUBLICATIONS

Bodnar et al, Biomacromolecules, 2005, 6, 2521-27.*
Brunel et al, Carbohydrate Polymers, 2013, 92, 1348-56.*
Qi et al, Carbohydrate Research, 2004, 339, 2793-2700.*
Gouda et al, J. Industrial Textiles, 2010, 39(3), 203-214.*
Appel, A. et al., 2013, "Frontiers, Opportunities, and Challenges in Biochemical and Chemical Catalysis of CO2 Fixation", Chemical Reviews, American Chemical Society, vol. 113, pp. 6621-6658.
Peterson, A. et al., 2010, How Copper Center for Atomic-scale Materials Design, Department of Physics, Technical University of Denmark, Energy Environmental Science, Article 3, pp. 1311-1315.
Perez, V.G. et al., Dec. 4, 2014, "Additivity of Effects From Dietary Copper and Zinc on Growth Performance and Fecal Microbiota of Pigs After Weaning", American Society of Animal Science, Journal of Animal Science, Article 879, pp. 414-425, doi:10.2527/jas.2010-2839.
Windle, Christopher D., and Perutz, Robin N., 2012, "Advances in Molecular Photocatalytic and Electrocatalytic CO2 Reduction", Coordination Chemistry Reviews, Article 256, pp. 2562- 2570, Elsevier B.V., doi:10.1016/j.ccr.2012.03.010.
Brugnerotto, J. et al., 2001, An Infrared Investigation in Relation With Chitin and Chitosan Characterization, Polymer, Article 42, pp. 3569-3580.
Condi de Godoi, F. et al., 2013, "An XPS Study of Chromate and Vanadate Sorption Mechanism by Chitosan Membrane Containing Copper Nanoparticles", Chemical Engineering Journal, Article 234, pp. 423-429.
Souli, M. et al., 2012, "Antimicrobial Activity of Copper Surfaces Against Carbapenemase-Producing Contemporary Gram-Negative Clinical Isolates", Journal of Antimicrobial Chemotherapy, Article 68, pp. 852-857, doi:10.1093/jac/dks473 Advance Access publication 9.

(Continued)

*Primary Examiner* — Ganapathy Krishnan
(74) *Attorney, Agent, or Firm* — Bond Schoeneck & King, PLLC; George McGuire

(57) ABSTRACT

Embodiments of the present disclosure provide for water-soluble chitosan particles, methods of making water-soluble chitosan particles, and methods of using water-soluble chitosan particles. In an embodiment, the composition of water-soluble chitosan particles can be used in drug delivery, tissue engineering, bioimaging, biosensing, catalysis, and antimicrobial applications.

19 Claims, 10 Drawing Sheets

(56) References Cited

OTHER PUBLICATIONS

Warnes, S. L. et al., Aug. 2010, "Biocidal Efficacy of Copper Alloys Against Pathogenic Enterococci Involves Degradation of Genomic and Plasmid Dnas", Applied and Environmental Microbiology, vol. 76, No. 16, pp. 5390-5401.
Gartner, C. et al., 2011, "Interplay Between Structure and Dynamics in Chitosan Films Investigated With Solid-State NMR, Dynamic Mechanical Analysis, and X-Ray Diffraction", American Chemical Society, Biomacromolecules Article 12, pp. 1380-1386.
Kuo, Chia-Hung et al., 2013, "Biofuel Cells Composed by Using Glucose Oxidase on Chitosan Coated Carbon Fiber Cloth", International Journal of Electrochemical Science, Article 8, pp. 9242-9255.
Li, Christina W., and Kanan, M. W., Apr. 24, 2014, "Electroreduction of Carbon Monoxide to Liquid Fuel on Oxide-Derived Nanocrystalline Copper", Macmillan Publishers Limited, Nature, vol. 508, pp. 504-521, doi:10.1038/nature13249.
Costentin, C. et al., Aug. 30, 2012, "Catalysis of the Electrochemical Reduction of Carbon Dioxide", The Royal Society of Chemistry, Chem. Soc. Rev., Article 42, pp. 2423-2436.
Han, Xin-Yan et al., 2012, "Changes In Small Intestinal Morphology and Digestive Enzyme Activity With Oral Administration of Copper-Loaded Chitosan Nanoparticles in Rats", Springer Science Business Media, LLC, Biol Trace Elem Res., Article 145, pp. 355-360, DOI 10.1007/s12011-011-9191-x.
Shukla, S. K. et al., 2013, "Chitosan-Based Nanomaterials: A State-Of-The-Art Review", Elsevier B.V., International Journal of Biological Macromolecules, Article 59, pp. 46-58.
Brunel, F. et al., Complexation of Copper II With Chitosan Nanogels: Toward Control of Microbial Growth, Elsevier Ltd., SciVerse ScienceDirect, Carbohydrate Polymers, Article 92, pp. 1348-1356.
Liu, C. et al., "Controllable Growth of Graphene/Cu Composite and Its Nanoarchitecture-Dependent Electrocatalytic Activity to Hydrazine Oxidation", Journal of Materials Chemistry A, Article 2, pp. 4580-4587.
Xiao, Z. et al., 2013, "Conversion of Highly Concentrated Cellulose to 1,2-Propanediol and Ethylene Glycol Over Highly Efficient Cucr Catalysts", RSC Publishing, Green Chemistry, Article 15, pp. 891-895.
Borkow, Gadi and Gabbay, Jeffrey, 2005, "Cooper As a Biocidal Tool", Current Medicinal Chemistry, Article 12, pp. 2163-2175.
Ding, Shi-Jin et al., 2001, "Copper Metallization of Low-Dielectric-Constant A-Sicof Films for ULSI Interconnects", Institute of Physics Publishing, Journal of Physics: Condensed Matter, Article 13, pp. 6595-6608.
Usman, M.S. et al., 2012, "Copper Nanoparticles Mediated by Chitosan: Synthesis and Characterization Via Chemical Methods", MDPI Open Access, Article 17, pp. 14928-14936, doi:10.3390/molecules171214928.
Liu, D. et al., 2012, "On the Impact of Cu Dispersion on CO2 Photoreduction Over Cu/Tio2", Elsevier B.V., Catalysis Communications, Article 25, pp. 78-82.
Richardson, R. D. et al., Apr. 2011, "A Renewable Amine for Photochemical Reduction of CO2", Nature Chemistry, Article, vol. 3, pp. 301-303.
Chen, Jin-Yi et al., 2007, "Depositing Cu2O of Different Morphology on Chitosan Nanoparticles by an Electrochemical Method", Elsevier Ltd., Sciene Direct, Carbohydrate Polymers, Article 67, pp. 623-629.
Takeda, Hiroyuki and Ishitani, Osamu, 2010, "Development of Efficient Photocatalytic Systems for CO2 Reduction Using Mononuclear and Multinuclear Metal Complexes Based on Mechanistic Studies", Elsevier B.V., Coordination Chemistry Reviews, Article 254, pp. 346-354.
Andrews, E. et al., 2013, "Electrochemical Reduction of CO2 At Cu Nanocluster / (1010) ZnO Electrodes", Journal of the Electrochemical Society, Article 160, vol. 11, pp. H841-H846.
Qu, X. et al., 2000, "Effect of Lactic/Glycolic Acid Side Chains on the Thermal Degradation Kinetics of Chitosan Derivatives", Elsevier Science Ltd., Polymer, Article 41, pp. 4841-4847.
Hori, Y., 2008, "Electrochemical CO2 Reduction on Metal Electrodes", Faculty of Engineering, Chiba University, Chiba 263-8522, Japan, Modern Aspects of Electrochemistry, No. 42, Springer, New York, pp. 1-101.
Huang, H. et al., 2013, "Enhanced Fluorescence of Chitosan Based on Size Change of Micelles and Application to Directly Selective Detecting Fe3+ In Human Serum", Elsevier B.V., Biosensors and Bioelectronics, Article 42, pp. 539-544.
Fen, Yap Wing and Mahmood, Mat Yunus Wan, 2011, "Evidence of Cu(II) Ion Interaction in Crosslinked Chitosan Thin Film From X-Ray Photoelectron Spectroscopy and Field Emission Scanning Electron Microscopy", David Publishing, Journal of Materials Science and Engineering B 1, pp. 584-590.
Pennings, Pleuni S., 2013, "HIV Drug Resistance: Problems and Perspectives", Infectious Disease Reports, vol. 5:s1e5, pp. 21-25.
Iwamoto, M. et al., 1980, "Ir Spectroscopic Determination of Conh Content in Highly Deacylated Chitosan", International Journal of Biological Macromolecules, vol. 2, Issue 5, pp. 323-324.
Kang, J. et al., 2010, "Systematic Study of Synergistic and Antagonistic Effects on Adsorption of Tetracycline and Copper Onto a Chitosan", Elsevier Inc., Journal of Colloid and Interface Science, Article 344, pp. 117-125.
Qiao, J. et al., 2014, "Formation of Cu Nanostructured Electrode Surfaces by an Annealing—Electroreduction Procedure to Achieve High-Efficiency CO2 Electroreduction", Elsevier B.V, Electrochemistry Communications, Article 38, pp. 8-11.
Ogura, Kotaro, 2013, "Electrochemical Reduction of Carbon Dioxide to Ethylene: Mechanistic Approach", Elsevier Ltd., Journal of CO2 Utilization 1, pp. 43-49.
Jayalakshmi, J., and Balasubramanian, K., 2008, "Cyclic Voltammetric Behavior of Copper Powder Immobilized on Paraffin Impregnated Graphite Electrode in Dilute Alkali Solution", International Journal of Electrochemical Science, Article 3, pp. 1277-1287.
Le, M. et al., 2011, "Electrochemical Reduction of CO2 to CH3OH at Copper Oxide Surfaces", Journal of the Electrochemical Society, Article 158, No. 5, pp. E45-E49.
Yin, M. et al., Jun. 10, 2005, "Copper Oxide Nanocrystals", American Chemical Society, Journal of the American Chemical Society, Article 127, pp. 9506-9511.
Warnes, S.L. et al, 2012, "Mechanism of Copper Surface Toxicity in *Escherichia Coli* O157:H7 and *Salmonella* Involves Immediate Membrane Depolarization Followed by Slower Rate of DNA Destruction Which Differs From That Observed for Gram-Positive Bacteriaemi-2677", Environmental Microbiology, Article 14, vol. 7, pp. 1730-1743.
Thompson, K. et al., 2008, "Processing, Products, and Food Safety: Microbial Ecology Shifts in The Ileum of Broilers During Feed Withdrawal and Dietary Manipulations", Poultry Science, Article 87, pp. 1624-1632, doi:10.3382/ps.2007-00324.
Pettit, Robin K. et al., Jul. 2005, "Microplate Alamar Blue Assay for *Staphylococcus* Epidermidis Biofilm Susceptibility Testing", American Society for Microbiology, Antimicrobial Agents and Chemotherapy, vol. 49, No. 7, pp. 2612-2617.
Weaver, L. et al., Aug. 2010, "Potential Action of Copper Surfaces on Meticillin-Resistant *Staphylococcus Aureus*", Journal of Applied Microbiology ISSN 1364-5072, Article 109, pp. 2200-2205.
Gouda, M., and Hebeish, A., Jan. 2010, "Preparation and Evaluation of Cuo/Chitosan Nanocomposite for Antibacterial Finishing Cotton Fabric", Journal of Industrial Textiles, vol. 39, No. 3, pp. 203-214.
Du, Wen-Li et al., Feb. 4, 2008, "Preparation, Characterization and Antibacterial Properties Against *E. Coli* K88 of Chitosan Nanoparticle Loaded Copper Ions", Nanotechnology, Article 19, No. 085707, pp. 1-5, doi:10.1088/0957-4484/19/8/085707.
Zheng, Y. et al., Jun. 2, 2006, "Preparation of Chitosan—Copper Complexes and Their Antitumor Activity", Elsevier Ltd., Bioorganic & Medicinal Chemistry Letters 16, pp. 4127-4129.
Hori, Y. et al., 1985, "Production of CO and CH4 in Electrochemical Reduction of CO2 At Metal Electrodes In Aqueous Hydrogencarbonate Solution", The Chemical Society of Japan, Chemistry Letters, pp. 1695-1698.
Hori, Y. et al., 1986, "Production of Methane and Ethylene in Electrochemical Reduction of Carbon Dioxide at Copper Electrode

(56) References Cited

OTHER PUBLICATIONS in Aqueous Hydrogencarbonate Solution", The Chemical Society of Japan, Chemistry Letters, pp. 897-898.
Ratner, Buddy D. and Castner, David G., 2009, "Electron Spectroscopy for Chemical Analysis", John Wiley & Sons, Ltd., Surface Analysis: The Principal Techniques, 2nd Edition, pp. 47-112.
Hans, M. et al., Dec. 10, 2013, "Role of Copper Oxides in Contact Killing of Bacteria", American Chemical Society, Langmuir, Article 29, pp. 16160-16166.
Poulston, S. et al., Aug. 16, 1996, "Surface Oxidation and Reduction of Cuo and Cuzo Studied Using XPS and XAES", John Wiley & Sons, Ltd., Surface and Interface Analysis, vol. 24, pp. 811-820.
Mao, S. et al., 2004, "The Depolymerization of Chitosan: Effects on Physicochemical and Biological Properties", Elsevier B.V., Science Direct, International Journal of Pharmaceutics, Article 281, pp. 45-54.
Macomber, Lee and Imlay, James A., Mar. 31, 2009, "The Iron-Sulfur Clusters of Dehydratases Are Primary Intracellular Targets of Copper Toxicity", PNAS, vol. 106, No. 20, pp. 8344-8349.
Keith, John A. and Carter, Emily A., Apr. 23, 2012, "Theoretical Insights Into Pyridinium-Based Hotoelectrocatalytic Reduction of CO2", ACS Publications, Journal of the American Chemical Society, Article 134, pp. 7580-7583.
Myneni, S. et al., 1998, "Vibrational Spectroscopy of Functional Group Chemistry and Arsenate Coordination in Ettringite", Geochimica et Cosmochimica Acta, vol. 62, No. 21/22, pp. 3499-3514.
Sun, Y. et al., Feb. 29, 2012, "Photoelectrochemical Reduction of Carbon Dioxide At Si(111) Electrode Modified by Viologen Molecular Layer With Metal Complex", The Chemical Society of Japan, Chemical Letters, No. 41, pp. 328-330, doi:10.1246/cl.2012.328.
Xiong, Z. et al., 2013, "Silicon Nanowire Array/Cu2O Crystalline Core—Shell Nanosystem for Solar-Driven Photocatalytic Water Splitting", Nanotechnology, No. 24: 265402, pp. 1-9.
Hu, Xilan et al., 2010 Synthesis, Structure and Property of Mixed-valence Tetranuclear Copper Complex [Cu2L2]*[Cu (pht)2]2, Acta Chimica Sinica, vol. 68, No. 6 pp. 487-492.

\* cited by examiner

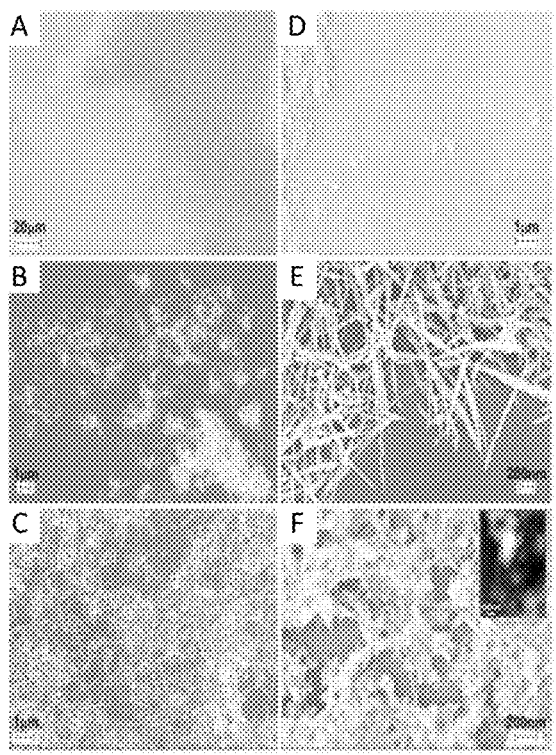
FIG. 1.1
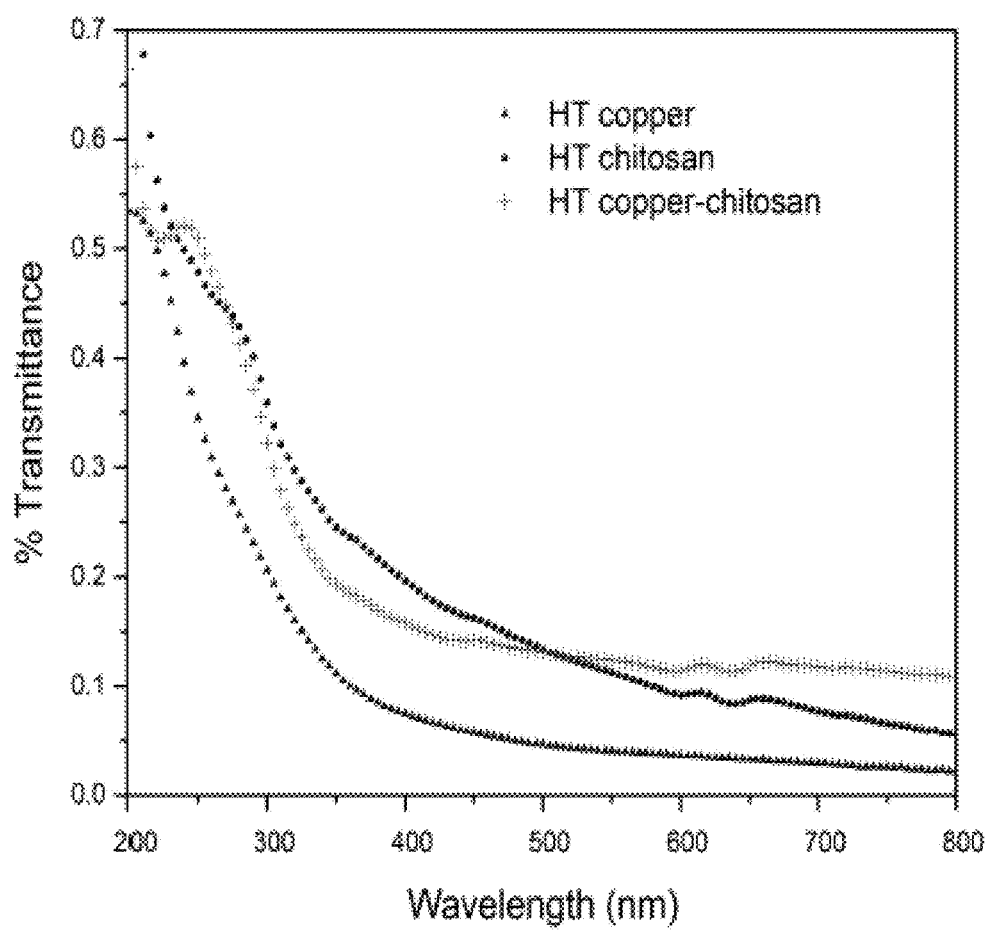
FIG. 1.2

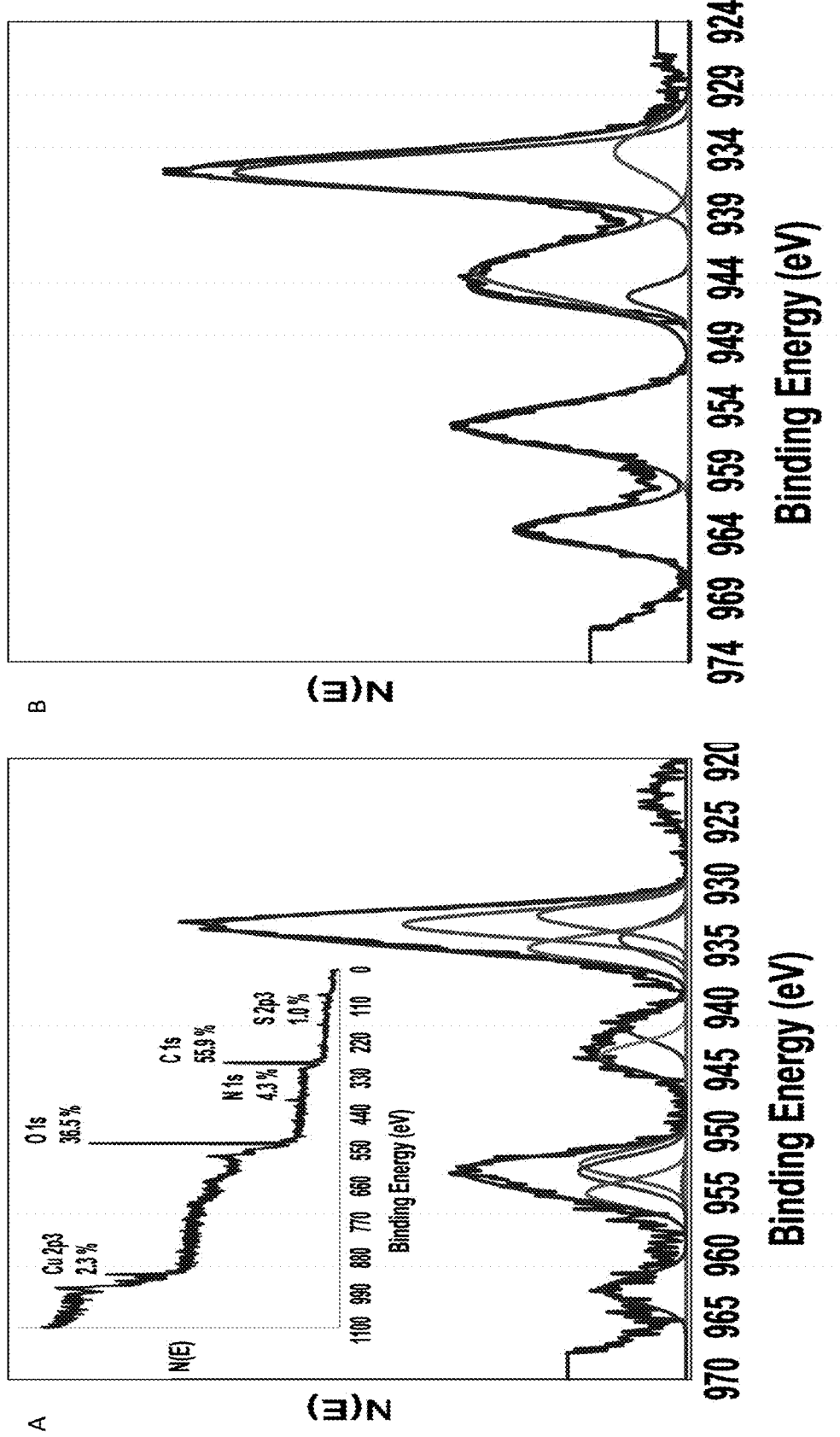
FIG. 1.3

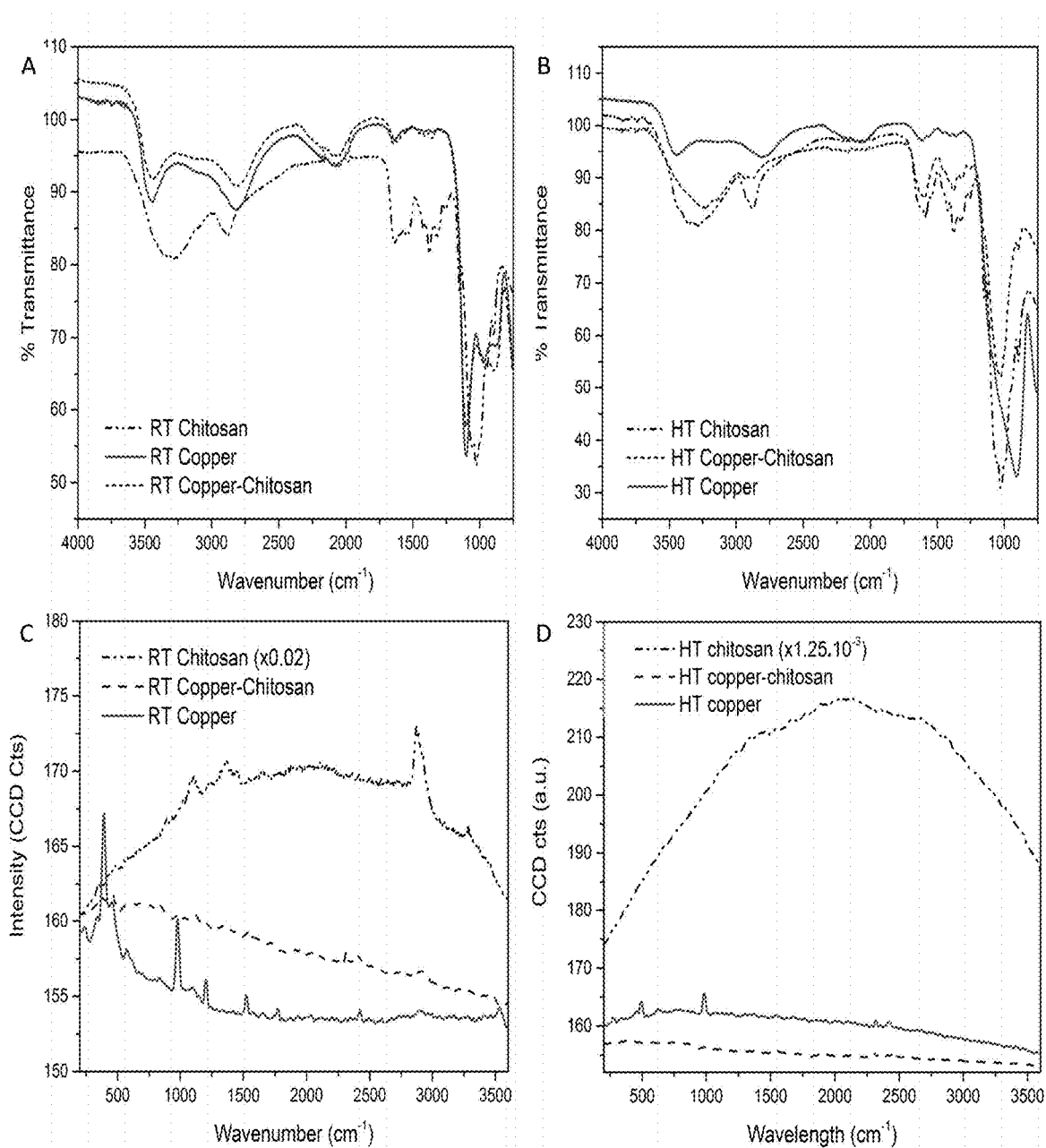
FIG. 1.4

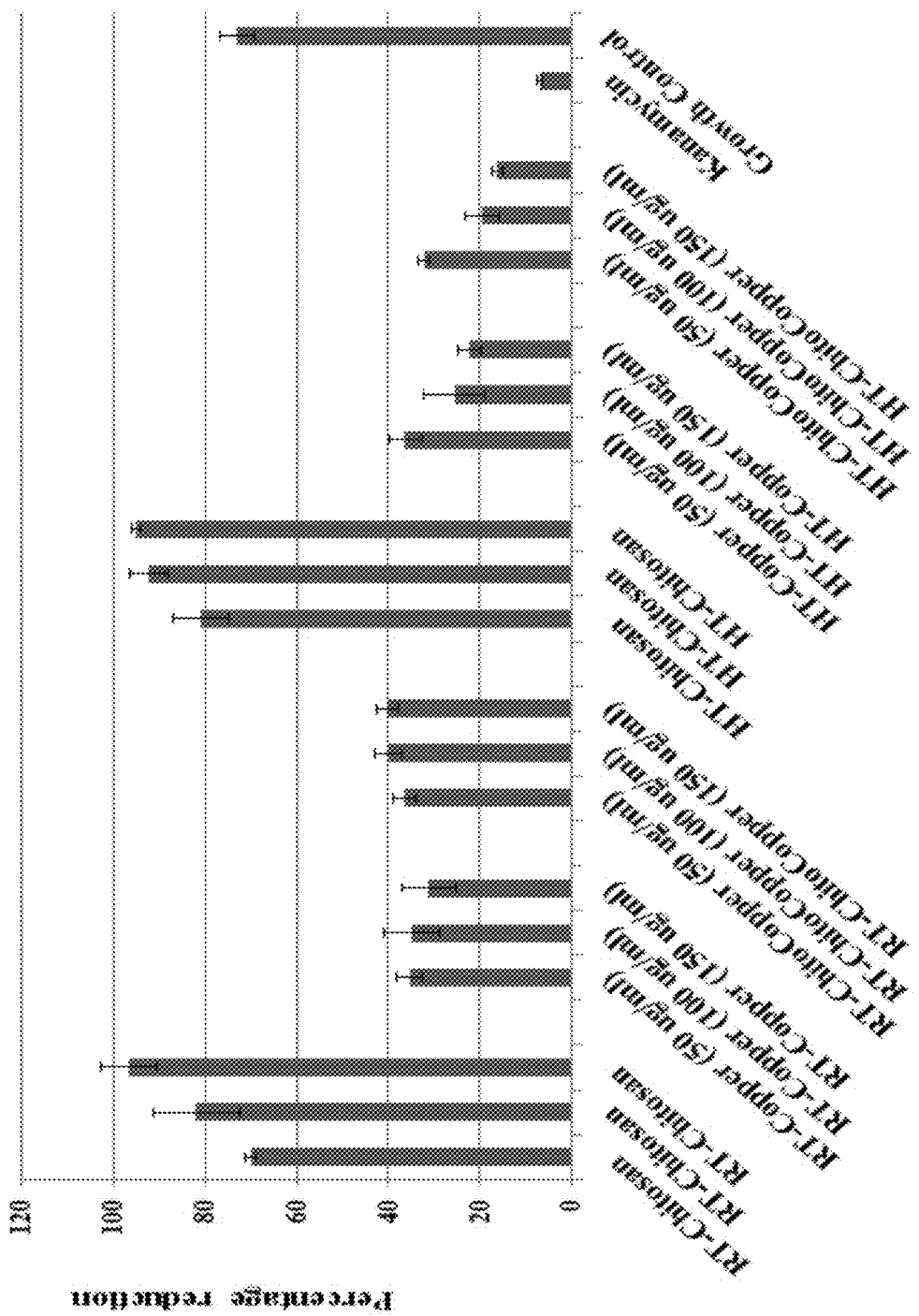
FIG. 1.5

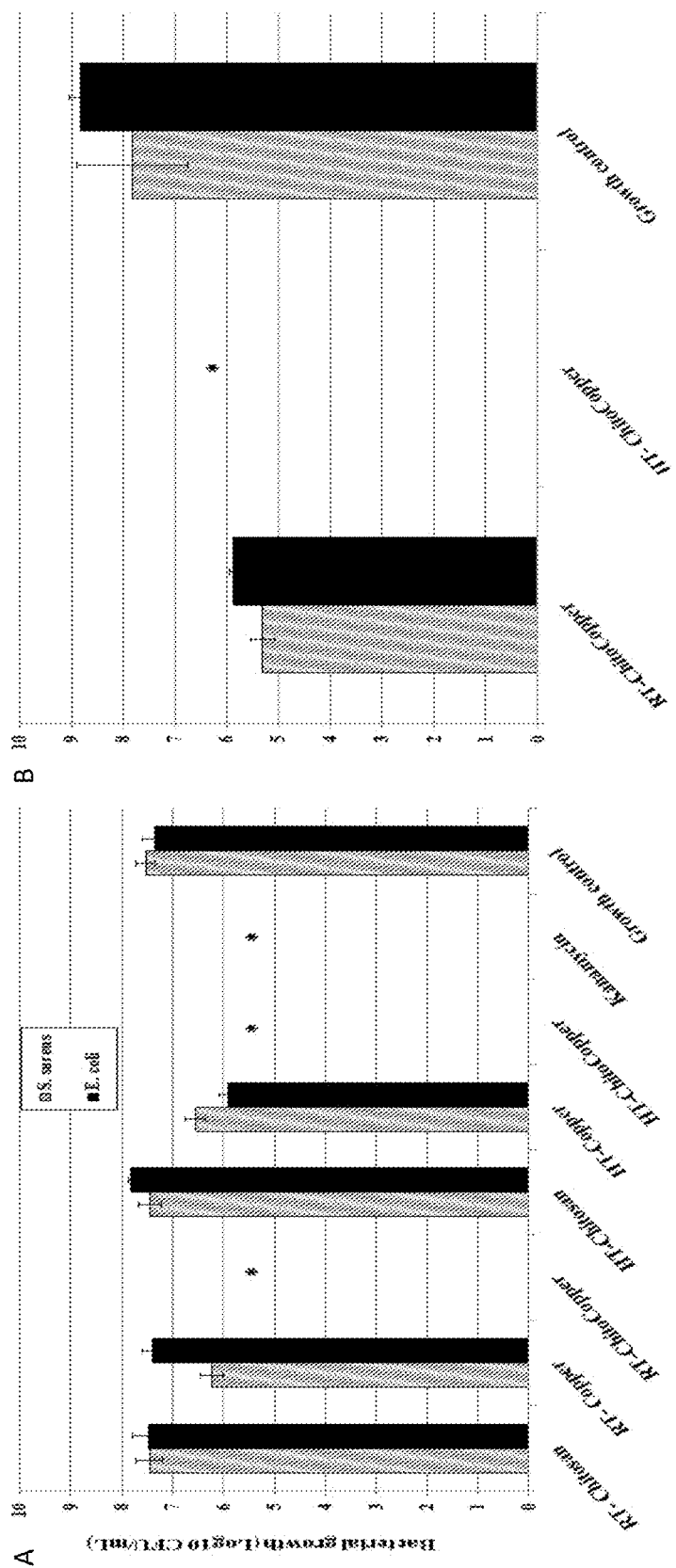
FIG. 1.6

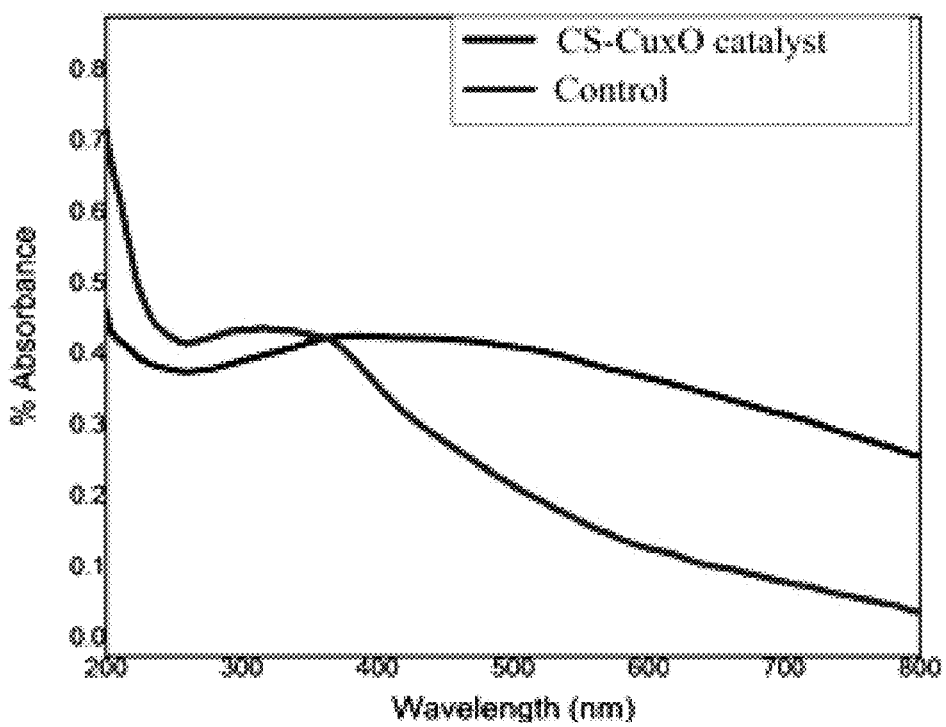
FIG. 2.1
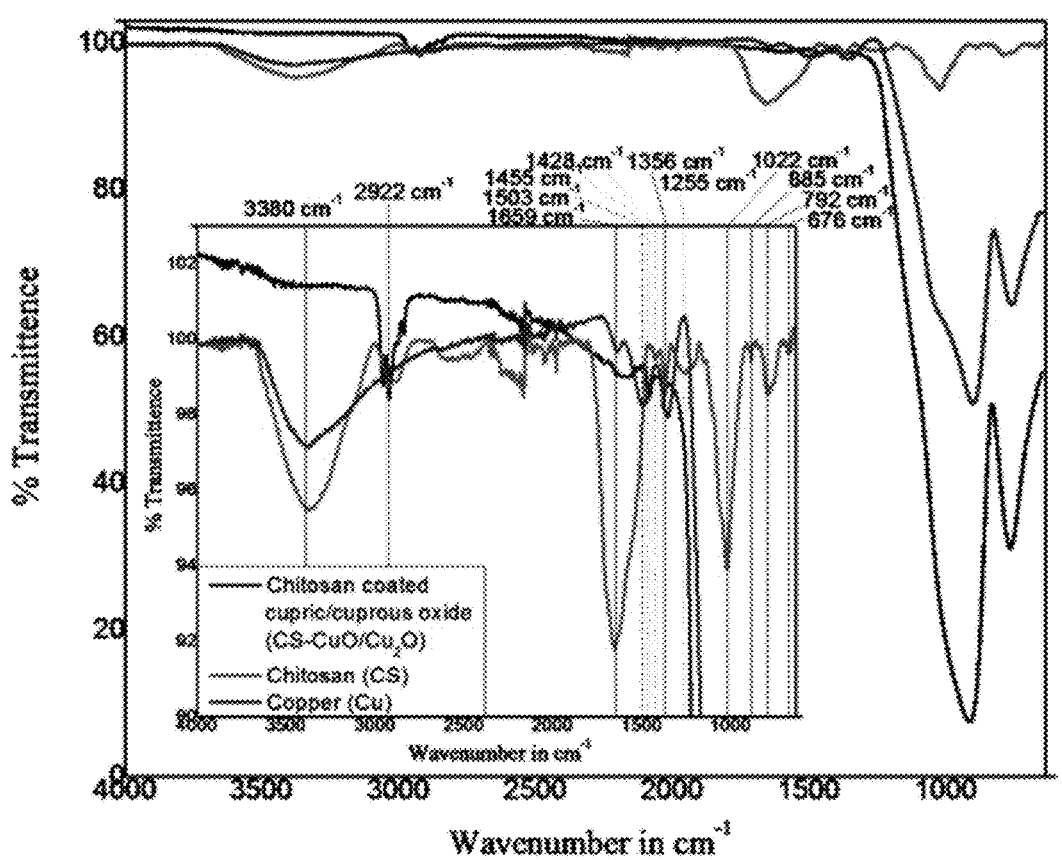
FIG. 2.2

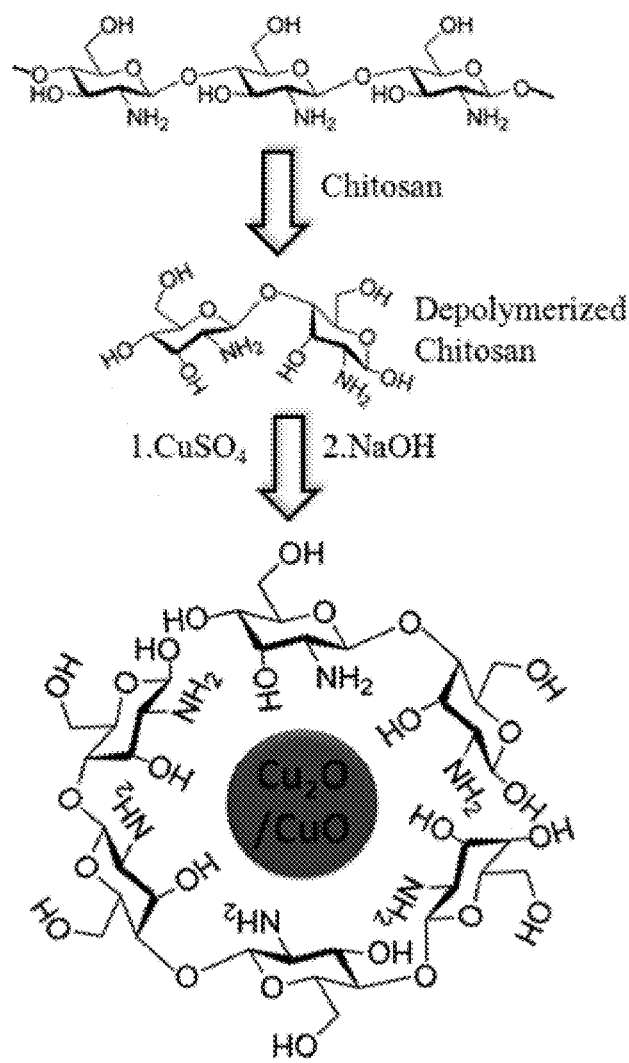
FIG. 2.3
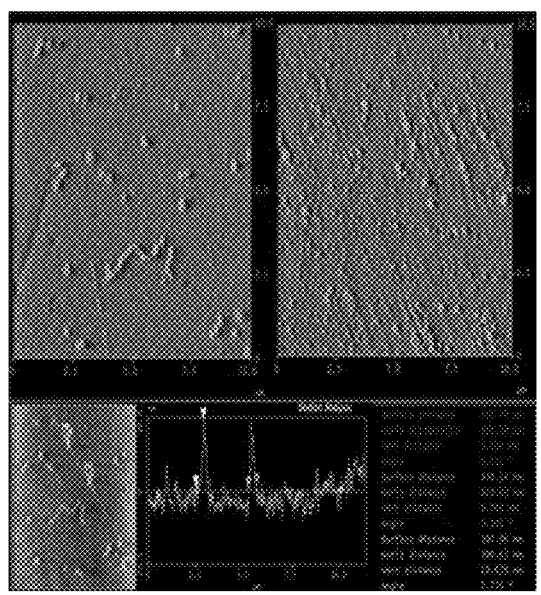
FIG. 2.4

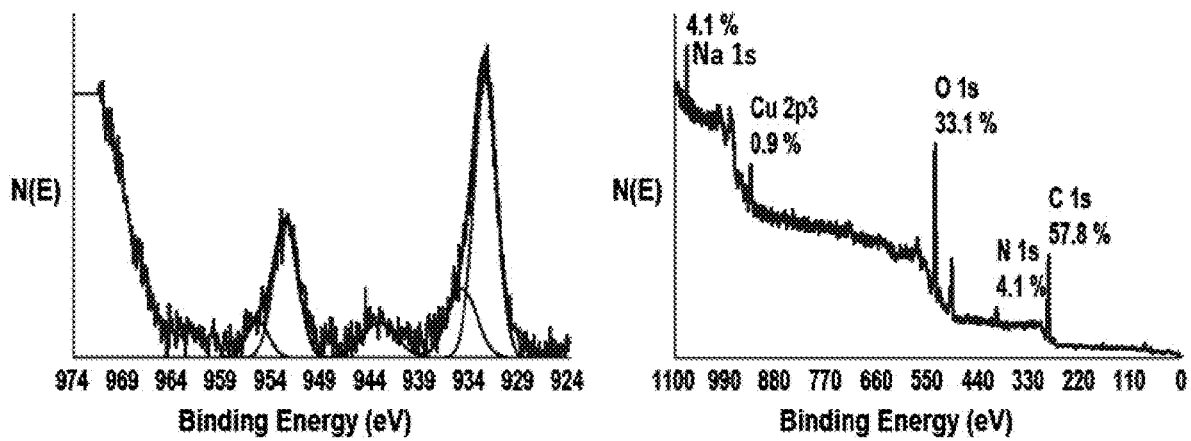
FIG. 2.5
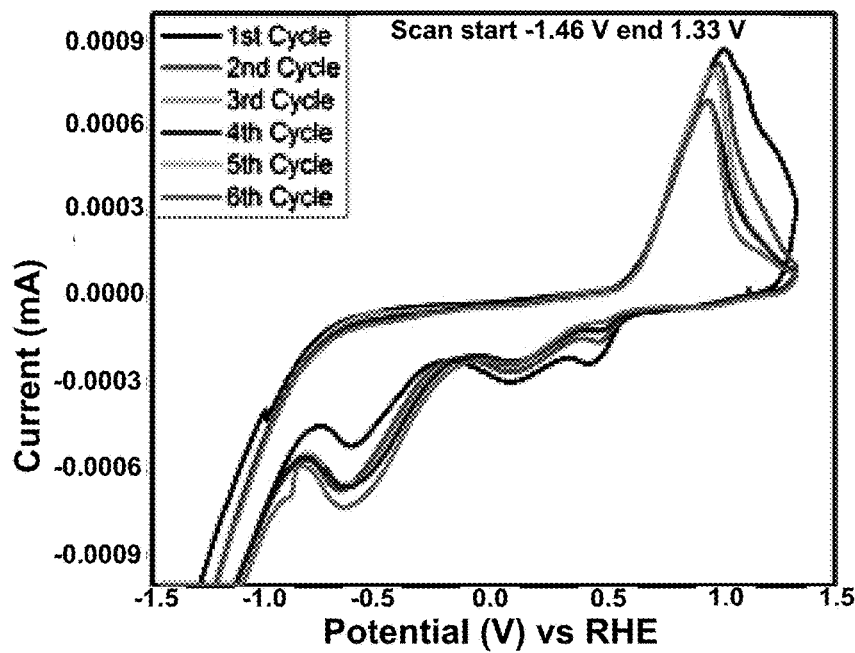
FIG. 2.6A

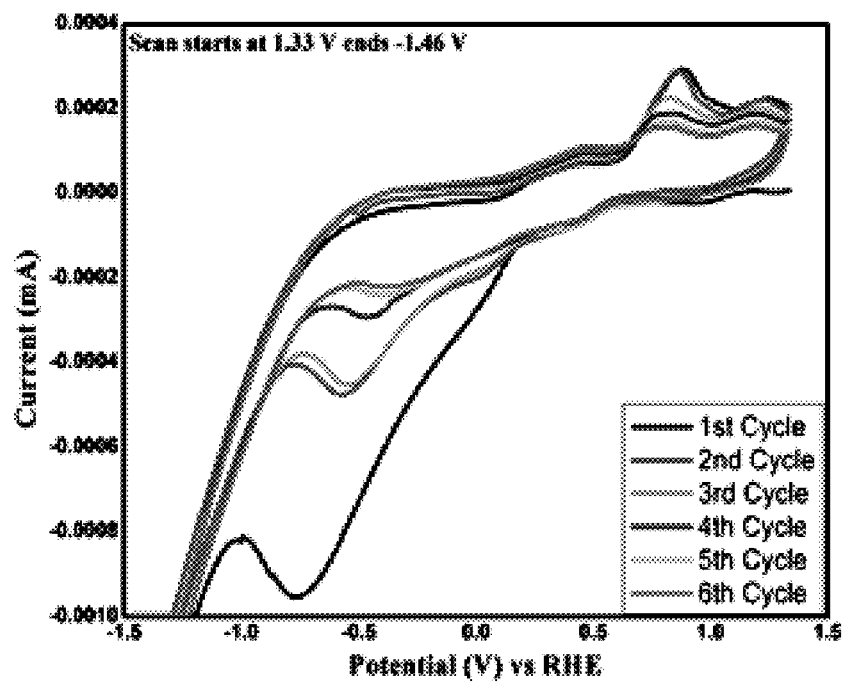
FIG. 2.6B
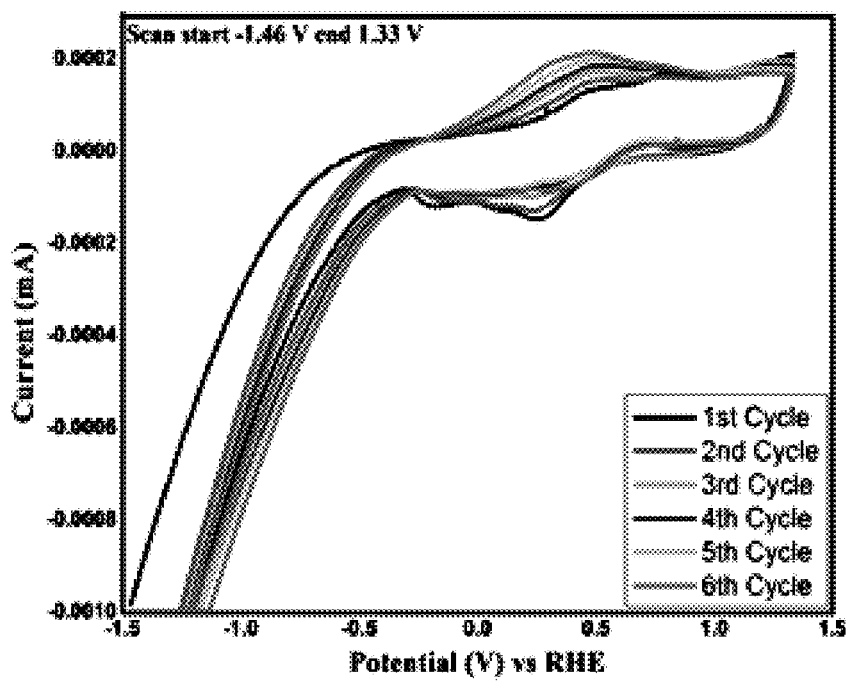
FIG. 2.7

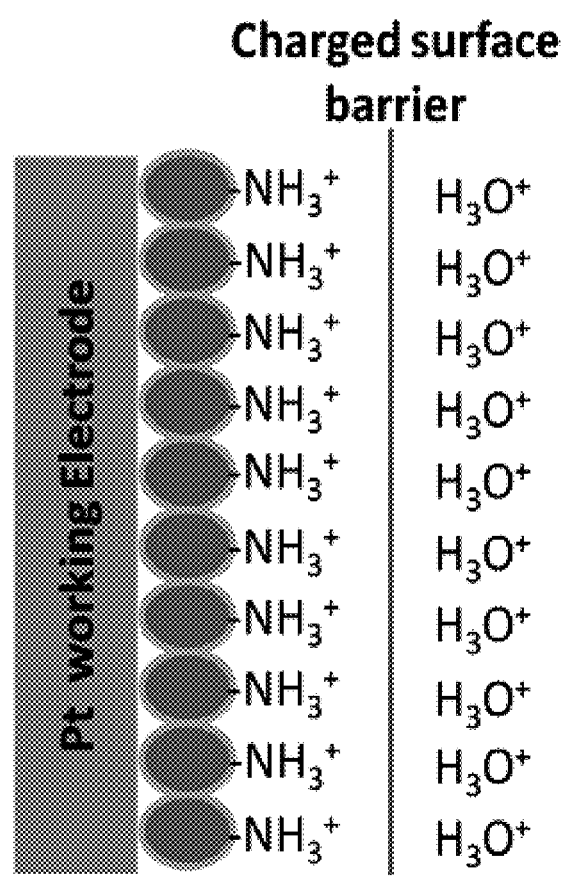
FIG. 2.8

COMPOSITION AND METHOD OF MAKING WATER SOLUBLE CHITOSAN POLYMER AND COMPOSITE PARTICLES

CLAIM OF PRIORITY TO RELATED APPLICATION

This application claims priority to U.S. provisional application entitled "COMPOSITION AND METHOD OF MAKING WATER SOLUBLE CHITOSAN POLYMER AND COMPOSITE PARTICLES" having Ser. No.: 61/992,510, filed on May 13, 2014, which is entirely incorporated herein by reference.

FEDERAL SPONSORSHIP

This invention was made with Government support under Contract/Grant No. 1159500, awarded by the National Science Foundation. The Government has certain rights in this invention.

BACKGROUND

Microbial resistance to conventional antibiotics constitutes a serious challenge in combating pathogens, particularly in case of life threatening infections. Combinatorial therapy containing multiple antibiotics is currently the most common strategy employed to minimize the incidence of drug resistance thus making the treatment regimen expensive. A potent and cheaper alternative to traditional antibiotics that has multiple mechanisms of action would reduce the total use of antibiotics and also would help in preventing any further development of microbial resistance. Copper compounds have been extensively used to protect crops from bacterial/fungal infections in agriculture and also as a prophylactic feed additive in livestock and poultry farms as a growth promoter. Copper exerts its antimicrobial effect via multiple modes of action including but not limited to cell membrane damage, protein chelation and enzyme deactivation.

SUMMARY

Embodiments of the present disclosure provide for water-soluble chitosan particles, methods of making water-soluble chitosan particles, and methods of using water-soluble chitosan particles. In an embodiment, the composition of water-soluble chitosan particles can be used in drug delivery, tissue engineering, bioimaging, biosensing, catalysis and antimicrobial applications.

An embodiment of the present disclosure includes a composition, among others, that includes: a water soluble chitosan particle, wherein the water soluble chitosan particle is an ionic complex of depolymerized chitosan (e.g., depolymerized chitosan oligomer, monomer, or a combination thereof) and a bicarboxylic acid compound. In an embodiment, the bicarboxylic acid compound is selected from the group consisting tartaric acid, malic acid, succinic acid, and a combination thereof. In an embodiment, the water soluble chitosan particle include a second component such as is copper or a copper compound.

An embodiment of the present disclosure includes a method of making a composition, among others, that includes: mixing a chitosan polymer and a bicarboxylic acid compound; and hydrothermal treating the mixture to form a water soluble chitosan particle, wherein the temperature is about 135 to 150° C., and the pressure of greater than 1 atm to about 5 atm.

BRIEF DESCRIPTION OF THE DRAWINGS

Many aspects of the present disclosure can be better understood with reference to the following drawings. The components in the drawings are not necessarily to scale, with emphasis instead being placed upon clearly illustrating the principles of the disclosure.

FIG. 1.1 illustrates a morphological study of the effect of hydrothermal treatment on chitosan, copper and copper-chitosan. Scanning Electron Microscopy (SEM) of (A) RT chitosan, (B) RT copper, (C) RT copper-chitosan, (D) HT chitosan, (E) HT copper, (F) HT copper-chitosan indicating significant changes in morphology as a result of HT treatment.

FIG. 1.2 illustrates UV-Vis spectroscopy of HT chitosan, HT copper, and HT copper-chitosan. The peak at 241 nm (black curve) indicate the presence of Cu(I) in HT copper-chitosan nanocomposite, while other peaks at 285 nm and 600 nm. analogous to HT chitosan, suggest that copper is embedded in the chitosan matrix FIG. 1.3 illustrates XPS of HT copper-chitosan (A) and HT copper, (B) demonstrate the presence of mixed valence copper Cu (I) and Cu (II) in the nanocomposite, both in free form and bound to chitosan. Corresponding survey spectrum is presented in inset FIG. 1.4 illustrates infrared spectroscopy of chitosan, copper, and copper-chitosan at RT (A, C) and after HT treatment (B, D). FT-IR spectra (A, B) clearly show a great change in copper-chitosan structure and chemical bonds after HT treatment, with the FT-IR spectrum changing from a RT copper- to a HT-chitosan like signature. Raman spectra (c, d) confirm the change in configuration resulting from HT treatment, with a great increase in the fluorescence background of HT chitosan and HT copper. However, HT copper-chitosan quenches the fluorescence of the individual components. The spectra also confirms change in copper configuration after HT treatment and when interacting with chitosan FIG. 1.5 illustrates alamar blue dye reduction test show that copper-chitosan (HT) elicit growth inhibition effect against Gram negative $E.$ $coli$. At metallic copper concentration of 150 µg/ml, the bacterial growth inhibition of (HT) copper-chitosan composite was similar to kanamycin. This test was used to screen for the most effective concentration that will be taken further for CFU assay FIG. 1.6 illustrates that copper-chitosan composite (both HT and RT) completely killed bacteria [both Gram negative ($E.$ $coli$) and Gram positive ($S.$ $aureus$)] at 150 µg/ml of metallic copper concentration (A). At the same concentration, neither chitosan nor copper had any significant bacterial growth inhibitory effect (A). But, at 100 µg/ml, only the HT copper-chitosan composite completely killed bacteria but the RT copper-chitosan did not kill completely (B) suggesting hydrothermal treatment enhances synergistic antimicrobial effect. Statistical significance of growth inhibition of candidate nanocomposite samples was compared with the growth control. (* indicates P<0.05)

FIG. 2.1 illustrates UV-Vis spectra of CS—$Cu_xO$ composite and a control.

FIG. 2.2 illustrates FTIR spectra of CS—$Cu_xO$ and its control.

FIG. 2.3 illustrates a schematic representation of chitosan coated CuO/$Cu_xO$ nano particles.

FIG. 2.4 illustrates AFM images of CS—$Cu_xO$ (top left) (particle diameter ~400 nm), thickness of the catalyst film (~18 nm, bottom) and AFM image of the control (top right).

FIG. 2.5 illustrates an XPS of CS—$Cu_xO$ (top, left) and $Cu_xO$, control (bottom), survey scan of CS—$Cu_xO$ (top, right).

FIG. 2.6A illustrates a CV of $CO_2$ reduction on to Pt|CS—$Cu_xO$ at a scan rate of 200 $mVs^{-1}$.

FIG. 2.6B illustrates a CV of $CO_2$ reduction onto Pt|ICS—$Cu_xO$ at scan rate of 200 $mVs^{-1}$.

FIG. 2.7 illustrates CV of $CO_2$ reductions onto Pt/$Cu_xO$ at a scan rate 200 $mVs^{-1}$.

FIG. 2.8 illustrates a schematic diagram showing positively charged barrier formation of CS coated $Cu_xO$ catalyst that retards $H_2$ evolution reaction.

DISCUSSION

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, synthetic organic chemistry, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in bar. Standard temperature and pressure are defined as 0° C. and 1 bar.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

General Discussion

Embodiments of the present disclosure provide for water-soluble chitosan particles, methods of making water-soluble chitosan particles, and methods of using water-soluble chitosan particles. In an embodiment, the composition of water-soluble chitosan particles can be used in drug delivery, tissue engineering, bioimaging, biosensing, catalysis, and antimicrobial applications.

Chitosan is a cationic biopolymer derived from chitin, the second most abundant natural polymer after cellulose. It has a strong potential for use in oral and nasal drug delivery systems due to its biocompatibility and mucoadhesive properties.

In an embodiment, the composition includes a water soluble chitosan particle. In addition to being water soluble, embodiments may be stable at a neutral pH. The water soluble chitosan particle can include an ionic complex of depolymerized chitosan and a bicarboxylic acid compound. In an embodiment, the depolymerized chitosan can include chitosan monomers, chitosan oligomers, or a combination of monomers and oligomers. In particular, the ionic complex (or composite) of monomers and/or oligomers and the bicarboxylic acid compound can be formed by ionic bonds between and/or among the chitosan monomers and/or oligomers and the bicarboxylic acid compound, where covalent bonds are not formed or very few are formed between the chitosan monomer and/or oligomers and the bicarboxylic acid compound in the complex as a whole. Although not intending to be bound by theory, the chitosan monomers and/or oligomers and the bicarboxylic acid compound form ionic bonds during self-assembly to form the ionic complex. In an embodiment, the ratio of depolymerized chitosan and the bicarboxylic acid compound in the ionic complex can be about 2:1 to 2.5:1.

In an embodiment, the water soluble chitosan particle can be spherical or semi-spherical. In an embodiment, the diameter (e.g., or longest dimension) can be about 10 to 100 nm or about 30 to 50 nm.

In an embodiment, the bicarboxylic acid compound can be tartaric acid, malic acid, succinic acid, and a combination thereof. In particular, the bicarboxylic acid compound can be tartaric acid.

In an embodiment, the water soluble chitosan particle can include one or more additional components. Although the additional component may not be separately water soluble, the water soluble chitosan particle including the additional component(s) can be water soluble.

The water soluble chitosan particle can include a metal or a metal compound (e.g., metal oxide). Although not intending to be bound by theory, the metal (e.g., charged or uncharged) and/or the metal compound can be chelated or coordinated with the ionic complex (e.g., form a complex with the bicarboxylic acid compound, the chitosan monomers, the chitosan oligomers, or a combination thereof). In an embodiment, the water soluble chitosan particle can include metals having different oxidative states (e.g., Cu(I) and Cu(II)). In another embodiment, the water soluble chitosan particles each can include metal having different oxidative states (e.g., Cu(I) and Cu(II)). In an embodiment, the metal present in the water soluble chitosan particle can include copper or a copper ion. In an embodiment, the water soluble chitosan particle can include $Cu_2O$, $CuO$, or a combination thereof. Inclusion of the copper in the water soluble chitosan particle can produce a water soluble chitosan particle that has antimicrobial properties.

In an embodiment, the additional component(s) can be about 35 to 85 or about 37.5 to 40 weight % of the water soluble chitosan particle complex. In particular, the metal, metal ion, or metal compounds can be about 35 to 85 or about 80 to 85 weight % of the water soluble chitosan particle complex.

In an embodiment, water-soluble chitosan particles can be synthesized using a one-step chemo-hydrothermal synthesis method. In this method, chitosan polymer and an appropriate bicarboxylic acid compound (e.g., tartaric acid) can be combined prior to the hydrothermal treatment. In an embodiment, the ratio of the chitosan polymer to bicarboxylic acid compound can be about 0.8:1.2 to 1.2:0.8. For example, the amount of chitosan polymer can be about 9.5 g/liter to 10.5 g/L, while the amount of bicarboxylic acid compound can be about 9.5 g/liter to 10.5 g/L. In an embodiment, the hydrothermal treatment includes heating the mixture to about 135 to 150° C. at a pressure of greater than 1 atm to about 2 atm, about 3 atm, about 4 atm, or about 5 atm for a time period of about 90 to 105 minutes.

When appropriate chemical cross-linker (e.g., bicarboxylic acid compound such as tartaric acid) is used this method can produce inherently fluorescent water-soluble chitosan particles. It should also be noted that the water-soluble chitosan particles possess primary amine groups that can be further utilized to conjugate cargoes for bioimaging applications. For example, an aldehyde group, acid chloride group, an acid anhydride group, can be bonded through use of the primary amine group.

In another embodiment, the chemo-hydrothermal synthesis method has been extended to synthesize water soluble chitosan particles that include an additional component such as a metal (e.g., Cu) or a metal compound (e.g., metal oxide). In an embodiment, the process is similar to that described above with the addition of the metal or metal compound to the mixture. The metal or metal compound can be formed within and/or on the surface of the water soluble chitosan particle. In an embodiment, the metal or metal compound is bound (e.g., ionically or covalently) to the water soluble chitosan particle).

Embodiments of the present disclosure have been characterized using UV-Vis, Fluorescence, FT-IR and 1NMR spectroscopy. Results from these studies suggested that water-soluble chitosan particle was improved due to introduction of more hydrophilic groups. AFM, SEM and DLS studies were done to characterize particle sizes and morphology of water-soluble chitosan particle including copper in both dry and aqueous states whereas XPS studies were done to determine Cu oxidation states (Cu(I) and Cu(II)). Additional details are provided in the Examples.

Embodiments of the present disclosure also have the ability to sequester carbon dioxide using an electrochemical setup, demonstrating catalytic properties of water soluble chitosan particles that include copper. The copper containing water soluble chitosan particles can serve as a catalyst for electrochemical reduction of $CO_2$ as it reduces hydrogen evolution reaction at high negative potential. Although not intending to be bound by theory, a possible model can include protonation of the amino group of the chitosan monomers and/or oligomers that repels the incoming proton towards a catalytic surface, which reduces hydrogen evolution reaction.

Embodiments of the present disclosure also have antibacterial characteristics. The antibacterial efficacy of water soluble chitosan particles containing copper have been tested using alamar blue assay, which showed a strong inhibition of antimicrobial growth against both Gram-negative and Gram-positive bacterial species in comparison to Cu precursor control. It was observed that mixed-valence Cu states (e.g., Cu(I) and Cu(II)) are present in water soluble chitosan particles containing copper, and this combination appears to play a role in exhibiting carbon dioxide sequestration and antimicrobial properties.

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

EXAMPLE 1

We report for the first time, a one-step hydrothermal (HT) process to design and synthesize water-dispersible chitosan nanoparticles loaded with mixed-valence copper. Interestingly, this HT copper-chitosan biocompatible composite exhibits exceptionally high antimicrobial properties. A comprehensive characterization of the composite indicates that the hydrothermal process results in the formation of monodispersed nanoparticles with average size of 40±10 nm. FT-IR and Raman spectroscopic studies unveiled that the hydrolysis of the glycoside bonds as the origin of the depolymerization of chitosan. Furthermore, X-Ray Photoelectron Spectroscopy measurements confirmed the presence of mixed-valence copper states in the composite, while UV-Vis and FT-IR studies revealed the chemical interaction of copper with the chitosan matrix. Hence, the extensive spectroscopic data provide strong evidence that the chitosan structure was rearranged to capture copper oxide nanoparticles. Finally, HT copper-chitosan composite showed a complete killing effect when tested against both Gram negative (*E. coli*) and Gram positive (*S. aureus*) bacteria at metallic copper concentration of 100 µg/ml. At the same concentration neither pure chitosan nor copper elicited such antimicrobial efficacy. Thus, we show that HT process significantly enhances the synergistic antimicrobial effect of chitosan and copper in addition to increasing the water-dispersibility.

Introduction:

Microbial resistance to conventional antibiotics constitutes a serious challenge in combating pathogens, particularly in case of life threatening infections (Pennings 2013). Combinatorial therapy containing multiple antibiotics is currently the most common strategy employed to minimize the incidence of drug resistance thus making the treatment regimen expensive (Pennings 2013). A potent and cheaper alternative to traditional antibiotics that has multiple mechanisms of action would reduce the total use of antibiotics and also would help in preventing any further development of microbial resistance. Copper compounds have been extensively used to protect crops from bacterial/fungal infections in agriculture (Borkow and Gabbay 2005) and also as a prophylactic feed additive in livestock and poultry farms as a growth promoter (Thompson et al. 2008; Perez et al. 2011). Copper exerts its antimicrobial effect via multiple modes of action including but not limited to cell membrane damage, protein chelation and enzyme deactivation (Macomber and Imlay 2009; Warnes et al. 2010; Warnes et al. 2012). We infer that a biocompatible composite material with improved copper bioavailability and enhanced antimicrobial efficacy has the potential to serve as a novel class of antimicrobial that would aid in minimizing the total use of conventional antibiotics thus could potentially reduce the incidence of drug resistance (Weaver et al. 2010; Souli et al. 2013). Of particular interest, a biocompatible copper based composite material would be a suitable improvement for topical wound healing and animal feed additive applications where conventional antibiotics are used as a preventive measure to contain infections.

Chitosan is a biocompatible matrix of polysaccharides that has attracted much interest in recent years for its drug delivery potential (Shukla et al. 2013). As a result, copper-chitosan complexes have been investigated for their synergistic effect in antibacterial (Gouda and Hebeish 2010), antitumor (Zheng et al. 2006) and plant protection (Brunel et al. 2013) studies. Various methodologies have been developed to incorporate copper into a chitosan matrix with an effective concentration for targeted effect while avoiding any toxicity on normal cells/tissues (Du et al. 2008; Gouda and Hebeish 2010; Han et al. 2012; Brunel et al. 2013). On the one hand, mixed valence copper has been examined for its potential for antimicrobial applications (Hu et al. 2010). Since all forms of copper (i.e. Cu(0), Cu(I) and Cu (II)) exhibit antimicrobial activity with varied efficacies (Hans et al. 2013), improving antimicrobial efficacy using a mixed valence copper system would be of great interest as it will enable multiple mechanisms of inducing bacterial cell death. On the other hand, native chitosan, a linear, long chain polymer of N-acetyl-D-glucosamine molecules is a high molecular weight molecule. Its water insolubility at neutral pH is a significant drawback for making an impact in biological applications under physiological conditions. Interestingly, chitosan of shorter chain length and lower molecular weight (LMW) can become water dispersible (Mao et al. 2004). Such LMW material is most commonly prepared by various depolymerisation methods including physical modification, chemical modification, chemical grafting or enzymatic digestion (Shukla et al. 2013). However, the enzymatic digestion and electromagnetic radiation processes used for such depolymerisation are expensive and labor intensive thus hindering their potential for scalable purposes.

The objective of the present study is to design a mixed valence copper system on a water dispersible LMW chitosan matrix where chitosan acts as (a) a reducing agent that converts part of Cu (II) into Cu (I), (b) a water soluble capping/stabilizing agent, and (c) a surface passivating agent that reduces any copper induced toxicity. We introduce a straightforward hydrothermal based procedure involving no purification steps to obtain water dispersible LMW chitosan. In addition, we show the first evidence of copper loading into LMW chitosan polymer and reduction of oxidation states to mixed valence copper states, in a single step, using hydrothermal treatment. Finally we present a comprehensive characterization of the synthesized new material as well as its potential as a microbiocide.

Materials and Methods:

Material Synthesis:

Room temperature (RT) copper-chitosan composites were prepared by adding 300 mg of commercial LMW water insoluble chitosan (Sigma Aldrich, St. Louis, Mo.) and 300 mg of copper sulfate pentahydrate ($CuSO_4.5H_2O$ technical grade, CQ concepts Inc., Ringwood, Ill.) into 30 ml of 1% hydrochloric acid (HCl technical grade, Fisher Scientific). The solution was stirred overnight and the pH was raised to 7.4 using 1N NaOH (ACS grade, Amresco, Solon, Ohio) the next day. Control samples including pure chitosan (300 mg of chitosan in 30 ml of 1% HCl) and pure copper (300 mg of copper sulfate in 30 ml of 1% HCl) were prepared similarly by stirring overnight and raising the pH to 7.4 the following day. For preparing hydrothermal (HT) copper-chitosan composites, 300 mg of LMW chitosan and 300 mg of copper sulfate pentahydrate were added into 30 ml of 1% hydrochloric acid. Next, the total volume was transferred into a teflon sealed stainless steel container and placed inside a pre-heated Lindeberg/Blue M oven (Thermoelectron corporation) at 150° C. for 90 minutes. Following hydrothermal depolymerization, the pH of the transparent product was raised to 7.4. Similarly, control samples (pure chitosan and pure copper) underwent the same hydrothermal treatment conditions and their pH was raised following depolymerization. The final products were further characterized and evaluated for their antimicrobial efficacy. From here in this manuscript, the final products of both HT and RT treated copper sulfate samples post raising the pH will be referred as HT copper and RT copper.

Material Characterization:

Spectroscopic Characterization:

UV-Vis absorption spectra of six samples (RT chitosan, HT chitosan, RT copper, HT copper, RT copper-chitosan, HT copper-chitosan) were measured using a Varian Cary 300 Bio UV-Vis spectrophotometer. Fourier Transform Infrared Spectroscopy (FT-IR, Perkin Elmer Spectrum 100 with attenuated total reflectance (ATR) module) was used to assess the effect of hydrothermal treatment and copper loading on chitosan chemical structure, in terms of its functional groups. The measurements were acquired in an ATR configuration, in the range 650 to 4000 $cm^{-1}$, with a resolution of 4 $cm^{-1}$ and step size 1 $cm^{-1}$. Raman spectra were obtained on WITec alpha300 RA under ambient conditions with excitation wavelength of 532 nm. The spectra were collected with 20 seconds acquisition time and 20 accumulations. X-Ray Photoelectron Spectroscopy (XPS) was performed on a Physical Electronics 5400 ESCA spectrometer equipped with a monochromatic Al Kasource operating at 300 W. Vision software provided by the manufacturer was used for data analysis and quantification. A Shirley background was used for quantification and curve fitting of Co2p, C1s, N1s and O1s spectra. All the spectra were charge referenced to the aliphatic carbon at 285 eV. For curve-fits, 70% Gaussian/30% Lorentzian line shape was used.

Microscopic Characterization:

Atomic Force Microscopy (AFM): AFM images of the various samples were acquired in AC mode (also known as tapping mode) at room temperature on a Witec Alpha 300 RA with aluminum coated silicon cantilever (AIOA Budget Sensor).

Scanning Electron Microscopy (SEM): Scanning electron microscope (Zeiss ULTRA-55 FEG) was used to characterize the morphology of samples that were spin-coated on boron-doped silicon wafers (Nova electronic materials, index of refraction 3.42 and resistivity 10 (Ω·m). The images were acquired at 8 kV.

Antibacterial Assays:

Microplate Alamar Blue Assay (MABA):

Antibacterial efficacy of the copper-chitosan nanocomposites was determined by studying the growth of *Escherichia coli* (ATCC 35218) and *Staphylococcus aureus* (ATCC 25923) strains subjected to copper-chitosan treatments of various concentrations. Bacterial growth inhibition was assayed in flat-bottom, polystyrene 96-well plates by measuring the alamar blue dye reduction using a Spectramax plate reader (Molecular devices) following standard protocols (Pettit et al. 2005). Briefly, bacterial cultures were grown at 37° C. in a shaking incubator (200 rpm) and harvested at exponential phase of the growth. The optical density (OD) was adjusted to 0.5 MacFarland standards to prepare a working stock. Bacterial cultures were added at 100 μl/well at a concentration of $2-4 \times 10^5$ CFU/ml. A sequence of concentrations of the test samples (in triplicates) were added thus making the total volume to 200 μl/well along with the bacterial culture. A triplicate of wells containing classical antibiotic kanamycin (50 μg/ml) served as the hallmark of bacterial killing. After 24 h of incubation at 37° C., 10 μl/well of alamar blue dye (Molecular probes, OR) was added to each well followed by incubation. After 60 minutes of incubation at 37° C., the absorbance of each well at both 570 nm and 600 nm were measured. Wells containing sterile media and alamar blue served as negative control. Alamar blue assays for each bacterial strain were conducted at least three times to verify the results for reproducibility.

The percentage reduction of the dye was calculated by using the following formula as supplied by the manufacturer:

$$\frac{(\varepsilon_{ox})_{\lambda_2} A_{\lambda_1} - (\varepsilon_{ox})_{\lambda_1} A_{\lambda_2}}{(\varepsilon_{red})_{\lambda_1} A'_{\lambda_2} - (\varepsilon_{red})_{\lambda_2} A'_{\lambda_1}} \cdot 100$$

Where $\varepsilon_{ox}$ is the molar extinction coefficient of Alamar blue oxidized form (blue), $\varepsilon_{red}$ the molar extinction coefficient of Alamar blue reduced form (pink), A the absorbance of test wells, A' the absorbance of negative control well, $\lambda_1=570$ nm, $\lambda_2=600$ nm Bacterial Killing Assay (CFU/ml):

The bacterial killing ability of the copper-chitosan nanocomposite was determined by colony forming unit (CFU) assay. The most effective concentration of copper (in the copper-chitosan nanocomposite), i.e. concentration with the highest growth inhibition observed in MABA (150 μg/ml), was used to perform the CFU assay. Treatment of bacteria with nanocomposite was carried out following the same procedure as described in the MABA assay. After 24 hours of nanoparticle treatment to the bacteria, each sample was serially diluted in phosphate buffered saline and plated on tryptic soy agar (TSA). After overnight incubation at 37° C., individual colonies were counted and expressed in logarithmic scale (base 10) for analysis. Three separate experiments were performed to assess the reproducibility of bacterial killing effect.

Statistical Analysis:

The difference in bacterial killing ability of the copper-chitosan nanocomposites was statistically analyzed using ANOVA and tukey's honestly significant difference methods. In all the experiments, P<0.05 was considered significant.

Results and Discussion:

Hydrothermal Treatment Facilitates Copper Loading by Altering the Morphology of Chitosan:

The morphology of the materials was determined using SEM and AFM imaging (FIG. 1.1). The SEM images clearly show a change in morphology of the chitosan from a film-like structure hardly detectable on the Si wafer before HT treatment (FIG. 1.1*a*), to well defined sub-50 nm nanoparticles after HT treatment (FIG. 1.1*d*). Similarly, we observed a major difference between the morphology of RT and HT copper-chitosan composites. While RT copper-chitosan (FIG. 1.1*c*) conserved the morphology of both individual RT rod shaped copper particles (FIG. 1.1*b*) and RT chitosan fine film/powder components (FIG. 1.1*a*), HT copper-chitosan (FIG. 1.1*f*) clearly formed nanoparticles in the sub-50 nm range. However, both RT and HT copper samples (FIGS. 1.1*b* and 1.1*e*, respectively) retained their rod-like shape. The HT copper-chitosan nanoparticle sizes were confirmed in the AFM images (see insets of FIG. 1.1*f*), in regions where the powder was not aggregated. The particle size was found to be in the range 40±10 nm.

Further, UV visible spectroscopic studies were done to investigate any changes in optical absorption properties of the HT copper-chitosan material with respect to controls (HT chitosan and HT copper). UV-Vis absorption spectra are presented in FIG. 1.2. The HT copper-chitosan shows a 241 nm absorption peak, indicative of the presence of Cu(I) species in the composite. The characteristic Cu(I) absorption peak usually appears at 260 nm. A blue shift of 19 nm in the absorption peak is suggestive of complex formation of Cu(I) species with HT chitosan. Other peaks at 285 nm and 600 nm coincide with the HT chitosan spectrum, suggesting that copper is associated with the chitosan matrix after HT treatment.

Copper Nanoparticles Loaded on to Chitosan Matrix Exhibit Mixed Valence States:

The mixed valence Cu(I) and Cu(II) states in HT copper-chitosan were verified by XPS (FIG. 1.3). The measurements were carried out for HT copper-chitosan and HT copper samples. The results presented in FIG. 1.3*a* show a reduction in Cu 2p shake-up peaks and Cu 2p peak due to the reduction of Cu(II) to Cu(I) in presence of chitosan. In addition, a decrease in the atomic concentration of Cu 2p could be observed, indicating surface coating of copper by chitosan (Mahmood 2011). Furthermore, a large asymmetric signal in the Cu 2p3/2 core region could be deconvoluted into four contributions at 932.6 eV (Poulston et al. 1996; Chen et al. 2007; Mahmood 2011), 934.5 eV (Ding et al. 2001; Mahmood 2011), 933.3 eV and 935.2 eV (Liu et al. 2014). It appears that the signals at 932.6 and 934.5 eV correspond to Cu (I) and Cu (II) peaks of $Cu_2O$ and $Cu(OH)_2/CuO$ particles formed in the composite respectively (29). The 933.3 and 935.2 eV can be attributed to chitosan-bound Cu(I) and Cu(II) peaks respectively (de Godoi et al. 2013). The high resolution core level C 1s spectra for HT copper-chitosan show three peaks that were absent for HT copper, and are representative of: (1) contaminated (glue residues) carbon or C—C chemical binding at 284.8 eV, (2) C—O, C—N or C—O—C bonds at 286.5 eV, confirming the binding to chitosan (Mahmood 2011), and (3) C═O or O—C—O chemical bindings (Beamson 1992; Briggs and Seah 1994; Ratner and Castner 2009; Xiao et al. 2013) of chitosan at 288.2 eV. Another peak at 530.5 eV also appeared in the XPS spectrum of HT copper-chitosan (not shown here), which further confirms the formation of a bond between C═O of N-acetylated-glucosamine in chitosan and Cu(II) (Mahmood 2011). These results strengthen our hypothesis that in addition to shortening the polymer chains of chitosan, HT treatment also enables the copper of mixed valence states to be captured into the chitosan matrix.

Hydrothermal Treatment Enhances Native Fluorescence of Chitosan and Rearranges the Structure of Chitosan to Capture Copper Nanoparticles:

To further understand any changes in chitosan chemical structure as a result of HT treatment and copper-chitosan interactions, we evaluated the FT-IR and Raman spectral properties of the nanocomposites. The Raman spectra clearly demonstrate the intense background signal of HT chitosan (FIG. 1.4d), with an increase of several orders of magnitude (note that the curve was rescaled for comparison purposes), in agreement with previous findings by Huang et al. (2013), although the precise origin of the phenomenon associated to the fluorescence background (broad emission) of the compound remains unclear. The RT chitosan spectrum (FIG. 1.4c) exhibits signs of methylene C—H stretching bond at 2878 $cm^{-1}$ (symmetric) and 2926 $cm^{-1}$ (asymmetric). Indications of incomplete methyl bond around 1300-1450 $cm^{-1}$ suggest chitosan deacetylation. Saturated ether (1104 $cm^{-1}$) and $NH_2$ stretching (3287 $cm^{-1}$) can also be identified. These bands could not be resolved in HT chitosan due to high level of fluorescence. FT-IR spectral information aided the detailed understanding of the IR active bands in the samples before (FIG. 1.4a) and after HT treatment (FIG. 1.4b). All compounds containing chitosan exhibit an amide band that is characteristic of chitosan with acetylated units (Brugnerotto et al. 2001). Direct comparison of the FT-IR signature of RT chitosan and HT chitosan show a change in hydrogen bonding at the 1651 $cm^{-1}$ bands. The change has previously been linked to reconfiguration of the free $NH_2$ (O'Neill 2011), as can also be seen from the change of the 1595 $cm^{-1}$ band. The C—H band at 1420 $cm^{-1}$ has been associated to the crystallinity of the structure and seems to be maintained after hydrothermal treatment. Similarly, C—O stretching peaks 1025 $cm^{-1}$ and 894 $cm^{-1}$ remain the same after HT. Although the C—O and C—H stretching bonds remain intact, the amplitude peaks changed significantly, confirming depolymerization. This agrees well with our prediction that during HT treatment, the chitosan polymeric chain was cleaved at the glycoside linkage joining sugar units (i.e. C—O—C bond hydrolysis) (Miya et al. 1980; Qu et al. 2000). The Raman spectra obtained for copper sulfate also show some indication of structural change after HT treatment. The SO (from $SO_4^{2-}$) stretching vibration could be observed at 1000 $cm^{-1}$ both before and after HT treatment while the anti-symmetric SO bands (1050 to 1200 cm-1) could not be found in HT copper. FTIR spectra of the RT copper and RT copper-chitosan show strong absorption of the O═S═O band around 1100 $cm^{-1}$, which corresponds to the IR stretching vibration of free $SO_4^{2-}$. Interestingly, these peaks disappeared after HT treatment. Instead a new peak around 900-950 $cm^{-1}$ indicates a change in the symmetry of the SO bonds (Myneni et al. 1998). More importantly, the spectrum of RT copper-chitosan exhibits features very similar to those of RT copper (FIG. 1.4a), while HT copper-chitosan resembles HT chitosan (FIG. 1.4b). Further, HT treatment on the composite modifies the configuration of O—H bonds as can be seen in the new profile of the peaks at ~3200 and ~3000 $cm^{-1}$ (FIG. 1.4b). Other changes in the 1000-1200 $cm^{-1}$ C—O stretching region and ~1400 $cm^{-1}$ could be observed, suggesting a significant rearrangement of the chitosan structure, which is in good agreement with the capture of copper into the chitosan nanoparticles (Usman et al. 2012).

Chitosan-Copper Nanocomposite Exhibits Superior Bactericidal Activity:

For initial screening of the composites for their antibacterial efficacy, microplate alamar blue assay (MABA) was used. Alamar blue assay employs an oxidation-reduction reaction to indicate the percentage of viable cells. The dye in its oxidized form is blue in color but turns into a pink color upon reduction. The color change can be observed either by naked eye or using absorbance and/or fluorescence detecting instruments. The percentage reduction is an indirect expression of concentration of viable bacteria as metabolic activity of the live bacteria changes the color of the dye by chemical reduction (Pettit et al. 2005). This semi-quantitative assay has been used as a rapid high-throughput screening test for a wide range of classical antimicrobials for their killing ability against clinical bacterial isolates (Pettit et al. 2005). Likewise, in our experiments, various concentrations of the copper-chitosan compounds (normalized for metallic copper ranging 50-800 μg/ml) were initially screened to detect bacterial growth inhibition ability using MABA assay. The second step involved the screening for the three most effective concentrations obtained from the first screening step (50-150 μg/ml) and is shown in FIG. 1.4. Thereby, we have demonstrated for the first time that MABA can be optimized to screen nanocomposites for their antimicrobial activity. For optimization of the protocol, we used both the results from the plate reader (for absorbance) and visual observation for analyzing the results to rule out any discrepancy in absorbance levels exhibited by the composites while determining the effective concentration for bacterial killing. Nevertheless, we have successfully adopted the MABA protocol to screen a large number of metal oxide nanocomposites at various concentrations for detecting bacterial growth inhibition. Additionally, this protocol allows us to narrow down the number of samples (most effective composite and its corresponding concentrations) that can be further tested for bacterial killing efficacy with CFU/viability assay. Kanamycin, a traditional antibiotic was used as a control for bacterial killing (at concentration 50 μg/ml). The wells with the most effective copper-chitosan concentration (150 μg/ml), were selected for CFU assay (FIGS. 1.5 and 1.6a). The reason behind picking this concentration is, as in this case, the killing (as visualized by the color) was comparable to that of observed for kanamycin treatment.

Both HT and RT copper-chitosan nanocomposites at a metallic copper concentration of 150 μg/ml completely killed both Gram negative *E. coli* and Gram positive *S. aureus* (FIG. 1.6a). But, at lower concentration (100 μg/ml), only HT copper-chitosan composite could completely kill bacteria (FIG. 1.6b). Interestingly, neither HT chitosan nor HT copper showed any growth inhibitory effect at those concentrations. Thus, we can deduce that the proposed one step hydrothermal treatment produces a HT copper-chitosan nanocomposite that not only facilitates synergistic activity between chitosan and copper, but also possesses an enhanced antibacterial efficacy when compared to the RT composite. We attribute this superior antimicrobial efficacy of HT copper-chitosan nanocomposite to smaller sized (30-50 nm) mixed valence copper oxide-chitosan nanoparticles that are uniformly dispersed across the solution. The increased surface area of these embedded copper oxide particles in the chitosan matrix allows for enhanced interaction with bacteria and therefore elicit a greater killing effect at lower concentrations. Contrarily, the RT samples killed bacteria only at a concentration of 150 μg/ml suggesting that unaltered morphology of either chitosan or copper (FIG. 1.3) limit antimicrobial efficacy at lower concentrations. Further, neither HT/RT chitosan nor HT/RT copper were able to demonstrate similar antibacterial effects at the concentrations that are considered here. Thus, the hydrothermal method of making copper-chitosan nanocomposite, incorporates the advantages of both producing uniform sized mixed valence copper-chitosan nanoparticles that are highly water dispersible and also eliciting antibacterial properties at a very low copper concentration (100 μg/ml). Alamar blue assays conducted on a separate set of nanocomposites that were washed with water (3 times) showed identical bacterial growth inhibition properties suggesting all the copper that was added in the reaction mixture were loaded on to the chitosan matrix and that there was no copper left unbound (data not shown). Therefore, we infer that HT method of making copper-chitosan composite facilitates metal (copper in this case) binding to the amino groups of chitosan polymer chains in such a way that it enhances antimicrobial efficacy. Studies underway in our laboratories are geared towards defining the nature of interaction between the nanoparticles and bacteria in order to thoroughly characterize the mechanism of killing by HT copper-chitosan composite.

CONCLUSIONS

Herein, we report a robust, one-pot synthesis of water dispersible chitosan produced by hydrothermal (HT) treatment from commercially available chitosan. We have demonstrated the mixed valence states of copper in the HT copper-chitosan nanocomposite, as well as its enhanced antimicrobial efficacy. Additionally, we have shown that HT treatment not only improves water dispersibility of chitosan but also enhances the antimicrobial effect of the copper-chitosan nanocomposite as it shows bacterial killing activity at lower concentration than the RT composite.

REFERENCES

EXAMPLE 2

We report here a simple one-pot method of synthesis of copper-oxide based novel film forming electro catalyst for $CO_2$ reduction. Water dispersible chitosan (CS)—CuO/$Cu_2O$ ($Cu_xO$) nano composites of diameter 10-20 nm was obtained by hydrothermal reactions of CS, $CuSO_4.5H_2O$ and tartaric acid (TA). Here, TA acts as a multifunctional reagent as de-polymerizer of CS, ionic cross linker of depolymerised CS and complex forming ligand with $Cu^{2+}$ ions. These CS coated $Cu_xO$ nanoparticles were characterized by HRTEM, UV-VIS, AFM, FTIR and XPS. An ultra thin film of composite catalyst was deposited onto a Pt electrode by drop cast technique and applied to study $CO_2$ reduction by cyclic voltametric technique. The voltammogram shows a reduction peak at –0.665 V vs. RHE at pH 5.3 with a short hydrogen evolution tail indicating its better performance in terms of retarding $H_2$ evolution reaction. This has been explained proposing a model of protonated CS on to electrode surface that repels incoming $H^+$ ion at the electrode-electrolyte interface. This is the first time we are reporting a film forming copper-oxide based nanocomposite material for efficient electro-catalytic reduction of $CO_2$ in aqueous solution.

Introduction:

During the recent years, there is an increasing interest[1-10] in the development of photo-catalysts and electro-catalysts for $CO_2$ reduction. Carbon dioxide is a greenhouse gas and a major contributor of global warming. Natural photosynthetic pathway or carbon pathway[11] is not capable of restoring the ecological $CO_2$ balance because of rapidly increasing global carbon emission. Thus, $CO_2$ utilization through its photo-chemical or electro-chemical reduction[1-10] is an additional effective path in restoring $CO_2$ balance. But major bottleneck of $CO_2$ reduction reaction is that it is an uphill reaction and kinetically difficult because of requirement of high activation energy. In natural photosynthetic dark reaction[11] free energy of cleavage of phosphate bond of ATP and reducing molecule NADPH are used to fix and reduce $CO_2$ to carbohydrate. The enzyme Ribulose Bisphosphate Carboxylase (RuBPCO) acts as catalyst. In laboratory experiments with $CO_2$ reduction using sun light or electrical energy, it is known oxides of copper;[5-7] particularly $Cu_2O$ is an efficient catalyst for such reduction. This is because of its unique crystalline structures[10, 12] where $CO_2$ molecules get easily adsorbed with favorable heat of adsorption.

In this example, we intend to focus on chitosan coated nano$Cu_xO$ composite catalyst for $CO_2$ reduction; we have selected chitosan as it has the ability to form an ultra thin adhesive film[13] onto electrode surface that will reduce catalyst loading. Chitosan loaded composite electrode has been successfully applied in immobilizing enzyme[14] for bio-fuel cells. Film forming ability of chitosan with linear chain structure has been studied[13] using solid-state NMR and X-ray diffraction techniques. These studies have revealed that H bonding ability of chitosan along with its strong cross linking ability through its protonated —$NH_2$ groups with polyvalent anion of a cross linker makes it an unique film forming material.

DFT calculations[12] on $CO_2$ reduction onto Cu based catalysts revealed different mechanistic paths for such reduction. These calculations have shown[12] possible mechanistic path for multi electron transfer reactions involve in $CO_2$ reduction.

Recently, Flake et al[15] reported Cu nano cluster loaded ZnO electrode for $CO_2$ reduction and shown that different reduction products as methane, CO, ethylene, methanol, ethanol, methyl formate are formed as reduction products. Hori et al[5-7] have shown $CH_4$ is the major product of $Cu_2O$ electrode surface. Again, it is reported[15] $CO_2$ reduction occurs within the potential range –0.6 to –1.4 V vs. Ag/AgCl or ~0.065 V to ~0.865 V vs RHE at pH 5.3. Usoki and his group[16] showed that at low over potential $CO_2$ reduction leads to formation of formic acid.

Ogura et al[10] in their review article discussed the mechanism of ethylene formation and pointed out that $CO_2$ is adsorbed onto Cu electrode prior to electro reduction.

In this example, we report a simple one-pot hydrothermal method of synthesis of chitosan coated nanocopper-oxide catalyst and studied their electro-catalytic activity towards $CO_2$ reduction. Chitosan is an excellent film forming material, it is anticipated CS coated $Cu_xO$ nanocomposite will be a promising catalytic material for efficient electro-reduction of $CO_2$. To the best of our knowledge this has not been reported earlier.

Experimental:
Materials:
Water insoluble low molecular weight Chitosan was purchased from Sigma Aldrich (Saint Louis, Mo., USA) and used without further treatment. $CuSO_4.5H_2O$, (technical grade) was purchased from CQ concepts INC (Ringwood, Ill., USA). NaOH (ACS grade, AmrescoSolon, Ohio, USA) and HCl (technical grade, Fisher Scientific.) were used as supplied. Hydrothermal reaction was carried out in a hard glass well stopper bomb keeping in a temperature controlled oven (Thermo electron corporation, Lundeberg/Blue M). A Mettler Toledo, Delta 320 pH meter was used to adjust pH of the solution after calibrating it using HACH pH calibration solutions. Barnsted Nano pure Diamond DI water was used to obtain DI water of resistivity 17.9 MΩcm. Fisher scientific Digital vortex mixers was used to mix reagents for reaction.

Preparation of Chitosan Coated Copper-Oxides Nanoparticles by Hydrothermal Method:

In this preparation of CS coated $Cu_xO$, we had optimised the reaction conditions for obtaining almost water dispersible (fewer agglomerated particles) product. Here, we took 300 mg of chitosan and 300 mg of tartaric acid that acts as depolymerizer, ionic cross linker and complex forming agent, in a hydrothermal bomb to that 30 ml of DI water was added, mixed well and kept at 150° C. under hydrothermal condition for 1.5 hours. After the reaction was over, the solution was cooled to room temperature and 25 ml of (1% w/v) $CuSO_4$ solution was added to the hydrothermally depolymerized solution and kept under vortex for one hour followed by addition of 1.0 N NaOH drop wise to adjust its pH to 7.4. Then, 5 ml of this solution was added to 25 ml DI water and kept under hydrothermal at 150° C. for one hour to convert remaining $Cu(OH)_2$ completely to $Cu_2O/CuO$. The final dispersed solution was dialysed centrifuged and dried under vacuum for further studies.

Preparation of Control $CuO/Cu_2O$ (Without CS):

We followed literature[17] protocol of preparation of copper-oxide nano, dissolving 300 mg of Cu-acetate (in 30 ml of 10% $CH_3COOH$ solution followed by hydrothermal reaction at 150° C. for 90 min and pH of the solution was adjusted to 7.4. This dispersion was dialyzed against DI water, centrifuged and dried under vacuum. It was proposed that Cu-acetate undergoes disproportionation reaction under hydrothermal condition forming Cu and CuO.

Preparation of Control CS Solution:

CS solution (1% w/v) in 1% (v/v) HCl was heated at 150° C. for 90 min. The pH of the solution was raised to 7.4 by adding 1.0 N NaOH drop wise to this depolymerized CS solution. The final solution was centrifuged and re-dispersed in DI water. The washing procedure was continued for 3 to 4 times. The solution was vortexed for 15 minutes between each centrifuge and washing step. The solid palate was vacuum dried for FT-IR analysis.

Characterization:

Ultraviolet-Visible Spectroscopy (UV-VIS): UV-VIS absorption spectra of the prepared catalysts and their controls have been taken in the range 200-800 nm using Varian Cary 300 Bio UV-Vis double beam spectrophotometer in a semi micro quartz cuvette with path length 10 mm.

Fourier Transform Infra-red Spectroscopy (FT-IR): FT-IR technique was used to characterize functional groups present in these four samples. FT-IR spectra were recorded on Perkin Elmer Spectrum 100 ATR FT-IR Spectrometer.

TEM Images: FEI Tecnai TEM with resolution 0.20 nm point to point, 0.102 nm per line was used. The machine was equipped with SEG with hot and cold stages and High angle annular dark field (HAADF) detector using Gatan Image Filter (GIF). The lyophilized catalyst powder was dispersed in ethanol. Au grid with carbon mass was directly dipped in to the solution and after absorption was dried under vacuum for 24 hr to remove any solvent.

AFM Images: Water dispersed sample was spin coated and dried in vacuum onto a silicon wafer (boron doped, purchased from Nova electronic materials). AFM images were recorded on a Veeco Manifold multimode V model (tapping mode) using silicon nitride tip (radius B 50 nm) attached to a cantilever (spring constant=0.032 Nm, oscillating frequency 0-600 kHz). AFM images were recorded at room temperature.

XPS images: X-Ray Photoelectron Spectroscopy (XPS) was done on a Physical Electronics 5400 ESCA spectrometer equipped with a monochromatic Al Kasource operating at 300 W. Vision software provided by the manufacturer was used for data analysis and quantification. A Shirley background was used for quantification and curve fitting of Cu2p, C1s, N1s and O1s spectra. All the spectra were charge referenced to the aliphatic carbon at 285 eV. For curve-fits, 70% Gaussian/30% Lorentzian line shape was used.

Fabrication of Cu—CS composite and control $Cu_2O$ loaded electrodes for CV studies: Catalyst loaded electrodes were prepared by conventional drop cast method. 100 uL of dispersed Cu—CS was added to a 1 $cm^2$ cleaned Pt electrode and the water was evaporated under vacuum. Similar procedure was followed to prepare control electrode. For cyclic voltammetry study, the catalyst loaded electrode was used as working electrode coupled with a Pt counter electrode and Ag/AgCl reference electrode. The electrodes were dipped into a solution taken in a beaker containing 10 ml of 0.1 M $Na_2SO_4$ solution saturated with $CO_2$, prepared just before the measurement by reaction of 2 ml 0.2 M $Na_2CO_3$ and 2 ml 0.2 M $H_2SO_4$. CV was recorded at a scan rate of 200 $mVs^{-1}$ in the potential window of +0.8 to −2.0 V, the CV diagrams are shown in FIG. 2.6-2.7. The potential values are plotted in RHE at pH 5.3 for the sake of comparison with literature data Results and Discussions:

FIG. 2.1 shows UV-visible spectra of CS coated copper-oxide nanoparticles and their control. A flat absorption peak around 450 nm with minima around 250 nm is seen. This featureless absorption behavior may be due to presence of both Cu (I) and Cu (II) oxides in the composites. It is interesting to note that the UV spectra of the control NPs show a sharp absorption peak at 250 nm. This may be attributable to the presence of uncoated Cu (I) oxide in the control.

IR spectra of these catalysts and their control are shown in FIG. 2.2. These are more or less similar to the reported spectra[18] CS coordinated copper complex. The broad peak around 3400 $cm^{-1}$ of CS due to —OH and —$NH_2$ stretching is reduced substantially in the CS coated catalyst due to its low concentration onto NM surface. However, presence of —CH stretching at 2900 $cm^{-1}$ in the spectra of catalyst clearly indicate that copper oxides NMs are capped with CS. Appearance of a carbonyl peak at around 1659 $cm^{-1}$ and amide (II) 1503 $cm^{-1}$ (blue shifted[18] because of capping) as well as characteristic amide (III) at 1356 $cm^{-1}$, reinforces presence of CS, together with this 1255 $cm^{-1}$, 1022 $cm^{-1}$, for glycosidic bond also indicates presence of chitosan. A pictorial representation of the CS coated nanomaterial is shown in FIG. 2.3. It is seen that depolymerized CS will easily bind to metal-oxide nanoparticles by ligand binding mode and will be dispersible in aqueous medium because of presence of hydrophilic groups.

AFM images of this catalyst and its control are shown in FIG. 2.4. It is seen that distinct non agglomerated particles of relatively smaller sizes are formed with catalyst in contrast to catalyst control where particles are mostly agglomerated. AFM image shows these NMs are composed of particles of different sizes as expected from their preparation method.

XPS images of CS—CuO/Cu$_x$O indicate presence of mixed valence states Cu (II) and Cu (I) on the surface. While Cu (I) state is predominating in CS—CuO/Cu$_x$O catalyst, Cu (II) oxide is present at a larger percentage on the surface of the control sample (FIG. 2.4). This may be owing to reducing property of CS. The peak at 932 eV and auger parameter 1848 eV is due to Cu 2p3/2 and characteristic of Cu (I) state. In survey spectra the peak for N 1s indicates presence of CS. Different functional groups present in chitosan help in coating formation as seen in C 1s as well as O 1s peaks.

HRTEM analysis shows formation of nanoparticles of core diameter 10-15 nm with d spacing of 4.2 Å (characteristic of Cu$_2$O, 111), these crystals also show presence of grain bounderies. Pt crystal with grain bounderies shows higher current density in I/V curve, we anticipate similar behaviour with our catalyst material. Theoritical calculations[12] on CO$_2$ adsorption onto Cu$_2$O crystal show most favourable adsorption occurson 111 plane of Cu$_2$O crystal. From SAED analysis, we find brightest ring due to 111 planes indicating these nano crystals will adsorb CO$_2$ easily. The chitosan film embedded Cu$_2$O catalyst are seen in low magnification.

Electro-catalytic activities of these CS—Cu oxides catalysts towards CO$_2$ reduction have been studied by cyclovoltammetry (CV) techniques. Cyclovoltamograms of CO$_2$ reduction using these catalyst loaded electrodes in 0.1 M Na$_2$SO$_4$ solution saturated with CO$_2$ (pH=5.3) at scan rate of 200 mVs$^{-1}$ are shown in FIG. 2.6-2.7, scan rate is optimized at 200 mVs$^{-1}$ to obtain significant peak current values and minimize Cu (II) formation during forward scan. A typical CV for this system using control catalyst at a scan rate of 50 mVs$^{-1}$ is shown in. Interestingly, the current values are reduced almost 10 folds compare to those at higher scan rate (FIG. 2.7); as a result, some important reduction peak like peak at −0.24 vs RHE of FIG. 2.7 become almost invisible. The appearance of initial small reduction peaks at around 0.535 V and 0.085 V vs RHE at pH 5.3 (FIG. 2.6) are owing to the reduction of Cu (II) to Cu and Cu (II) to Cu (I) respectively. These values are close to the reported values of these redox couples on to Cu powder pasted on graphite electrodes.[19]

Cyclovoltamograms of CO$_2$ reduction using different electro-catalysts including Cu$_2$O, Cu—ZnO composite have been reported[20] earlier that shows a long downward cathodic tail[20] due to H$_2$ evaluation reaction (HER) along with a small CO$_2$ reduction peak. We have also observed similar cathodic tail[20] owing to H$_2$ evaluation reaction (HER) with our Cu$_2$O control without CS (FIG. 2.7).

But with CS composites of Cu$_x$O, this tail appears (FIG. 2.6) after −0.865 V with a small peak at −0.665 V vs RHE at pH 5.3 attributable to CO$_2$ reduction. This indicates HER onto CS—Cu oxides composite surface is retarded probably due to protonation of free amino groups of CS which repels incoming H$^+$ towards electrode surface as shown in FIG. 2.8. It is interesting to note that basic features of the clyclovoltammogram remains unaltered after repeating the cycles and changing the scanning directions which indicate that the catalysts are not poisoned by the reduction products.

Carpenter et al[21] reported that an indole based amine acts as a good photo catalyst for conversion of CO$_2$ to formic acid.

Flake et al[15(a)] has reported good Faradic efficiency for CO$_2$ reduction onto Cu—ZnO surface holding potential at −1.4 V vs Ag/AgCl and in another paper[15(b)] this group has pointed out that thinner copper-oxide layers are found to improve efficiency of CO$_2$ electro-reduction to methanol. Ogura et al[10] pointed out that CO$_2$ reduction starts at −0.6 V vs Ag/AgCl and formation of hydro-carbons like ethelene, methane etc occur at −1.2 V vs Ag/AgCl. It is well reported that CO$_2$ reduction potential, onset and cathodic peak potential dependent on the reaction conditions[15(b)] like pH of the solution, composition and morphology of the catalyst[22] as these factors mainly dictate the reaction path and products of the reactions. Generally, mixtures of different products as CO, HCOOH, CH$_3$OH, CH$_4$, CH$_2$=CH$_2$ etc are formed[5, 6, 10, 15] during such electro reduction process owing to multi steps electro-chemical (EC) and chemical mechanistic paths.[11] It is reported[15] CH$_3$OH is the major reduction product onto Cu$_2$O surface though it involves six electron transfer reaction.

$$CO_2(g) + 6H^+ + 6e^- = CH_3OH(aq) + H_2O$$

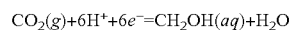

$E_0 = +0.02$ V vs SHE

From FIG. 2.6, it is seen that CO$_2$ reduction starts at −0.075 V vs RHE at pH 5.3 or +0.025 V vs SHE with a peak potential at −0.665 V vs RHE, indicating possible formation of mixture of products including methanol as the observed potential is close to the reported value of oxidation potential of methanol onto Cu$_2$O surface. We have repeated the experiment several times using freshly prepared CS—Cu oxides catalyst and successively using the catalyst coated electrodes, we got an excellent reproducible results indicating stability of the CS coated catalyst and its control. Here, we have not found any signature of methanol oxidation peak at the anodic scan; this may be due to extremely low methanol concentration on the electrode surface. Methanol formation as a major product of CO$_2$ reduction onto Cu2O surface is well reported.[11, 15] and augments our analysis on onset potential of CV experiment In aqueous environment the H$_2$ evolution reaction cannot be eliminated.[23] H$_2$ so formed may undergo dissociative adsorption onto catalytic surface[11] promoting chemical reduction path. In our control experiment with Cu$_x$O prepared using literature protocol, we found a small peak at −0.24 V vs RHE that is because of electro-reduction of adsorbed CO$_2$ in a different path as suggested by Ogura.[10]

CONCLUSIONS

In this example, we have prescribed a simple method of one-pot synthesis of 10-20 nm sizes CS coated CuO/Cu$_2$O nano electro-catalyst for CO$_2$ reduction. We have demonstrated for the first time that CS—Cu$_x$Onano composite is an ultra thin film forming electro-catalyst for CO$_2$ reduction in aqueous media and it retards hydrogen evolution reaction. This suggests CS—CuO/Cu$_2$O is a new thin film forming composite electro-catalyst for efficient CO$_2$ reduction.

REFERENCES

1 C. Costentin, M. Robert and J. M. Save'ant, *Chem. Soc. Rev.*, 2013, 42, 2423

2 H. Takeda and O. Ishitani, *Coord. Chem. Rev.*, 2010, 254, 346.

3 D. Windle and R. N. Perutz, *Coord. Chem. Rev.*, 2012, 256, 2562.

4 J. A. Keith and E. A. Carter, *J. Am. Chem. Soc.*, 2012, 134, 7580.

5 Y. Hori, K. Kikuchi and S. Suzuki, *Chem. Lett.*, 1985, 1695.

6 Y. Hori, K. Kikuchi, A. Murata and S. Suzuki, *Chem. Lett.*, 1986, 897.

7 Y. Hori, in Modern Aspects of Electrochemistry, ed. C. G. Vayenas, R. E. White and M. E. Gamboa-Aldeco, Springer, New York., 2008, 42, 89.

8 Z. Xiong, M. Zheng, S. Liu, L. Maand W. Shen, *Nanotechnology.*, 2013, 24, 265402.

9 D. Liu, Y. Fernandez, O. Ola, S. Mackintosh, M. Maroto, V. Christopher, M. A. Parlett, A. F. Lee and J. C. S. Wu, *Catal. Commun.*, 2012, 25, 78.

10 K. Ogura, *Journal of $CO_2$ Utilization.*, 2013, 1, 43.

11 A. M. Appel, J. E. Bercaw, A. B. Bocarsly, H. Dobbek, D. L. DuBois, M. Dupuis, J. G. Ferry, E. Fujita, R. Hille, P. J. A. Kenis, C. A. Kerfeld, R. H. Morris, C. H. F. Peden, A. R. Portis, S. W. Ragsdale, T. B. Rauchfuss, J. N. H. Reek, L. C. Seefeldt, R. K. Thauer and G. L. Waldrop, *Chem. Rev.*, 2013, 113 (8), 6621.

12 A. A. Peterson, F. Abild-Pedersen, F. Studt, J. Rossmeisl and J. K. Norskov, *Energy Environ. Sci.*, 2010, 3, 1311.

13 C. Gartner, B. López, L. Sierra, R. Graf, H. Spiess and M. Gaborieau, *Biomacromolecules.*, 2011, 12 (4), 1380.

14 C. Kuo1, W. Huang, C. Lee, Y. Liu, C. Chang, H. Yang, and C. Shieh, *Int. J. Electrochem. Sci.*, 2013, 8, 9242.

15(a) E. Andrews, M. Ren, F. Wang, Z. Zhang, P. Sprunger, R. Kurtz and J. Flake, *J. Electrochem. Soc.*, 2013, 160 (11), 841; (b) M. Le, M. Ren, Z. Zhang, P. T. Sprunger, R. L. Kurtz, and J. C. Flake, *J. Electrochem. Soc.*, 2011, 158 (5), 45.

16 Y. Sun, T. Masuda, and K. Uosaki, *Chem. Lett.*, 2012, 41 (3), 328.

17 M. Yin, C. Wu, Y. Lou, C. Burda, J. T. Koberstein, Y. Zhu and S. Brien, *J. Am. Chem. soc.*, 2005, 127, 9506.

18 J. Kang, H. Liu, Y. M. Zheng, J. Qua and J. P. Chen, *J. Colloid. Interf. Sci.*, 2010, 344, 117.

19 M. Jayalakshmi and K. Balasubramanian, *Int. J. Electrochem. Sci.*, 2008, 3, 1277.

20 M. Le, M. Ren, Z. Zhang, P. T. Sprunger, R. L. Kurtz and J. C. Flakea, *J. Electrochem. Soc.*, 2011, 158 (5), 45.

21 D. Robert, E. Richardson, J. Holland and B. Carpenter, *Nat. Chem.*, 2011, 3, 301.

22 J. L. Qiao, P. Jiang, J. S. yuiou Liu and J. J. Zhang, *Electrochem. Commun.*, 2014, 38, 8.

23 C. W. Li, J. Ciston and M. W. Kanan, *Nature.*, 2014, 508, 504.

24 Beamson, GBD (1992) High resolution XPS of organic polymers: the Scienta ESCA 300 database. Wiley, Chichester [England]; New York.

25 Borkow, G and Gabbay, J (2005) Copper as a biocidal tool. Curr. Med. Chem.12: 2163-2175.

26 Briggs, D and Seah, P (1994) Practical Surface Analysis: Auger and X-ray photoelectron spectroscopy. Wiley.

27 Brugnerotto, J., Lizardi, J., Goycoolea, F. M., Arguelles-Monal, W., Desbrieres, J. and Rinaudo, M. (2001) An infrared investigation in relation with chitin and chitosan characterization. Polymer 42:3569-3580. Doi 10. 1016/S0032-3861(00)00713-8.

28 Brunel, F., El Gueddari, N. E. and Moerschbacher, B. M. (2013) Complexation of copper(II) with chitosan nanogels: toward control of microbial growth. Carbohydr. Polym. 92:1348-1356. Doi 10.1016/j.carbpol.2012.10.025.

29 Chen, J-Y, Zhou, P-J, Li, J-L and Li, S-Q (2007) Depositing Cu2O of different morphology on chitosan nanoparticles by an electrochemical method. Carbohydrate. Polymers. 67:623-629. Doi 10.1016/j.carbpol.2006.07.003.

30 de Godoi, F. C. , Rodriguez-Castellon, E., Guibal, E. and Beppu, M. M. (2013) An XPS study of chromate and vanadate sorption mechanism by chitosan membrane containing copper nanoparticles. Chemical Engineering Journal 234:423-429. Doi 10.1016/j.cej. 2013.09.006.

31 Ding, S. J., Zhang, Q. Q., Zhang, D. W., Wang, J. T. and Lee, W. W. (2001) Copper metallization of low-dielectric-constant a-SiCOF films for VLSI interconnects. *Journal of Physics*-Condensed Matter 13:6595-6608. Doi 10.1088/0953-8984/13/31/301.

32 Du, W-L, Xu, Y-L, Xu, Z—R and Fan, C-L (2008) Preparation, characterization and antibacterial properties against E-*coli* K(88) of chitosan nanoparticle loaded copper ions. Nanotechnology 19:10.1088/0957-4484/19/8/085707.

33 Gouda, M. and Hebeish, A. (2010) Preparation and Evaluation of CuO/Chitosan Nanocomposite for Antibacterial Finishing Cotton Fabric. *Journal of Industrial Textiles* 39:203-214. Doi 10. 1177/1528083709103142.

34 Han, X-Y, Du, W-L, Huang, Q-C, Xu, Z—R and Wang, Y-Z (2012) Changes in Small Intestinal Morphology and Digestive Enzyme Activity with Oral Administration of Copper-Loaded Chitosan Nanoparticles in Rats. Biological Trace Element Research 145:355-360. Doi 10. 1007/s12011-011-9191-x.

35 Hans, M., Erbe, A., Mathews, S., Chen, Y., Solioz, M. and Mucklich, F. (2013) Role of copper oxides in contact killing of bacteria. Langmuir 29:16160-16166. 10. 1021/Ia404091z.

36 Hu, X. L., Shi, P. F., Xu, X. Y., Yin, FJ, Yang, Q and Wang, DQ (2010) Synthesis, Structure and Property of Mixed-valence Tetranuclear Copper Complex $[Cu_2L_2]$ center dot[Cu(pht)(2)](2). Acta Chimica *Sinica* 68: 487-492.

37 Huang, H., Liu, F., Chen, S., Zhao, Q., Liao, B., Long, Y., Zeng, Y. and Xia, X. (2013) Enhanced fluorescence of chitosan based on size change of micelles and application to directly selective detecting Fe(3)(+) in human serum. Biosens. Bioelectron 42: 539544. Doi 10.1016/j.bios.2012.10.098.

38 Liu, C., Zhang, H., Tang, Y. and Luo, S. (2014) Controllable growth of graphene/Cu composite and its nanoarchitecture-dependent electrocatalytic activity to hydrazine oxidation. *Journal of Materials Chemistry A* 2:4580-4587. Doi 10.1039/C3TA14137C.

39 Macomber, L. and Imlay, J.A. (2009) The iron-sulfur clusters of dehydratases are primary intracellular targets of copper toxicity. Proc. Natl. Acad. Sci. USA 106: 83448349. Doi 10.1073/pnas.0812808106.

40 Mahmood, Y.W. and Fa, M. Y. W. (2011) Evidence of Cu(II) Ion Interaction in Crosslinked Chitosan Thin Film from X-Ray Photoelectron Spectroscopy and Field Emission Scanning Electron Microscopy. *Journal of Materials Science and Engineering B* 5: 584-590.

41 Mao, S., Shuai, X., Unger, F., Simon, M., Bi, D. and Kissel, T. (2004) The depolymerization of chitosan: effects on physicochemical and biological properties. Int. J. Pharm. 281: 45-54. Doi 10.1016/j.ijpharm.2004.05.019.

42 Miya, M., Iwamoto, R., Yoshikawa, S. and *Mima*, S. (1980) Ir Spectroscopic Determination of Conh Content in Highly Deacylated Chitosan. International *Journal of Biological Macromolecules* 2:323-324. Doi 10.1016/0141-8130(80)90056-2.

43 Myneni, S. C. B., Traina, S. J., Waychunas, G. A. and Logan, T. J. (1998) Vibrational spectroscopy of functional group chemistry and arsenate coordination in ettringite. Geochimica. Et. Cosmochimica Acta 62:3499-3514. Doi 10.1016/S00167037(98)00221-X 44 O'Neill, A. N. and Fa, A. G. (2011) Focus on Chitosan Research. Nova Science Publishers, Incorporated, 45 Pennings, P. S. (2013) HIV Drug Resistance: Problems and Perspectives. Infect. Dis Rep 5:e5. Doi 10.4081/idr.2013.sl.e5.

46 Perez, V. G., Waguespack, A. M., Bidner, T. D., Southern, L. L., Fakler, T. M., Ward, T. L., Steidinger, M. and Pettigrew, J. E. (2011) Additivity of effects from dietary copper and zinc on growth performance and fecal microbiota of pigs after weaning. J. Anim. Sci. 89: 414-425. Doi 10.2527/jas.2010-2839.

47 Pettit, R. K., Weber, C. A., Kean, M. J., Hoffmann, H., Pettit, G. R., Tan, R., Franks, K. S. and Horton, M. L. (2005) Microplate Alamar blue assay for *Staphylococcus epidermidis* biofilm susceptibility testing. Antimicrob. Agents. Chemother. 49: 2612-2617. Doi 10.1128/AAC.49.7.2612-2617.2005.

48 Poulston, S., Parlett, P. M., Stone, P. and Bowker, M. (1996) Surface oxidation and reduction of CuO and Cu2O studied using XPS and XAES. Surface and Interface Analysis 24: 811-820. Doi 10.1002/(sici)1096-9918(199611)24:12<811::aid-sia191>3.0.co;2-z.

49 Qu, X., Wirsen, A. and Albertsson, A. C. (2000) Effect of lactic/glycolic acid side chains on the thermal degradation kinetics of chitosan derivatives. Polymer 41: 4841-4847. Doi 10.1016/S0032-3861(99)00704-1.

50 Ratner, B. D. and Castner, D. G. (2009) Electron Spectroscopy for Chemical Analysis, John Wiley & Sons, Ltd, 47-112.

51 Shukla, S. K., Mishra, A. K., Arotiba, 0. A. and Mamba, B. B. (2013) Chitosan-based nanomaterials: a state-of-the-art review. Int. J. Biol. Macromol. 59: 46-58. Doi 0.10.1016/j.ijbiomac.2013.04.043.

52 Souli, M., Galani, I., Plachouras, D., Panagea, T., Armaganidis, A., Petrikkos, G. and Giamarellou, H. (2013) Antimicrobial activity of copper surfaces against carbapenemase-producing contemporary Gram-negative clinical isolates. J. Antimicrob. Chemother. 68: 852-857. Doi. 10.1093/jac/dks473.

53 Thompson, K., Burkholder, K., Patterson, J. and Applegate, T. J. (2008) Microbial ecology shifts in the ileum of broilers during feed withdrawal and dietary manipulations. Poult. Sci. 87:1624-1632. Doi 10.3382/ps.2007-00324.

54 Usman, M. S., Ibrahim, N. A., Shameli, K., Zainuddin, N. and Yunus, W. M. Z. W. (2012) Copper Nanoparticles Mediated by Chitosan: Synthesis and Characterization via Chemical Methods. Molecules 17:14928-14936. Doi 10.3390/Molecules171214928.

55 Warnes, S. L., Caves, V. and Keevil, C. W. (2012) Mechanism of copper surface toxicity in *Escherichia coli* 0157:H7 and *Salmonella* involves immediate membrane depolarization followed by slower rate of DNA destruction which differs from that observed for Gram-positive bacteria. Environ. Microbiol. 14:1730-1743. Doi 10.1111/j.1462-2920.2011.02677.x.

56 Warnes, S. L., Green, S. M., Michels, H. T. and Keevil, C. W. (2010) Biocidal efficacy of copper alloys against pathogenic enterococci involves degradation of genomic and plasmid DNAs. Appl. Environ. Microbiol. 76:5390-5401. Doi 10.1128/AEM.03050-09.

57 Weaver, L., Noyce, J. 0., Michels, H. T. and Keevil, C. W. (2010) Potential action of copper surfaces on meticillin-resistant *Staphylococcus aureus*. J. Appl. Microbiol. 109: 22002205. Doi 10.1111/j.1365-2672.2010.04852.x.

58 Xiao, Z., Jin, S., Pang, M. and Liang, C. (2013) Conversion of highly concentrated cellulose to 1,2-propanediol and ethylene glycol over highly efficient CuCr catalysts. Green Chemistry 15: 891-895. Doi 10.1039/c3gc40134k.

59 Zheng, Y., Yi, Y., Qi, Y. P., Wang, Y. T., Zhang, W. A. and Du, M. (2006) Preparation of chitosan-copper complexes and their antitumor activity. Bioorganic & Medicinal Chemistry Letters 16: 4127-4129. Doi 10.1016/J.Bmc1.2006.04.077.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

The invention claimed is:

1. A composition comprising: a water-soluble chitosan nanoparticle, wherein the water-soluble chitosan nanoparticle comprises an ionic complex of a composite of a bicarboxylic acid compound, a metal oxide having mixed valence states and a depolymerized chitosan, the depolymerized chitosan comprising chitosan oligomers, chitosan monomers, or a combination thereof wherein each chitosan component of the depolymerized chitosan has a molecular weight that is less than 50,000 Da.

2. The composition of claim 1, wherein the bicarboxylic acid compound is selected from the group consisting tartaric acid, malic acid, succinic acid, and a combination thereof.

3. The composition of claim 1, wherein the metal oxide is bonded within the composite of the depolymerized chitosan and the bicarboxylic acid compound.

4. The composition of claim 1, wherein the metal oxide is is oxide of copper.

5. The composition of claim 4, wherein copper in the metal oxide has an oxidation state of a combination of Cu(I), Cu(II).

6. The composition of claim 4, wherein the water-soluble chitosan nanoparticle has antimicrobial properties.

7. The composition of claim 4, wherein the metal oxide is not separately water soluble, while the water soluble chitosan nanoparticle and the metal oxide combination is water soluble.

8. A method of making a composition, comprising:
mixing a chitosan polymer, a metal oxide having mixed valence states and a bicarboxylic acid compound, the chitosan polymer having a molecular weight of from about 50,000 Da to about 190,000 Da; and hydrothermal treating of the mixture to form a water-soluble chitosan nanoparticle, wherein the temperature utilized in the hydrothermal treatment is about 135 to 150° C., and the pressure of the hydrothermal treatment is greater than 1 atm and up to 5 atm, the water-soluble chitosan nanoparticle comprises a composite of a bicarboxylic acid compound and a depolymerized chitosan, the depolymerized chitosan comprising chitosan oligomers, chitosan monomers, or a combination thereof, wherein each chitosan component of the depolymerized chitosan has a molecular weight that is less than 50,000 Da.

9. The method of claim 8, wherein the bicarboxylic acid compound is selected from the group consisting of: tartaric acid, malic acid, succinic acid, and a combination thereof.

10. The method of claim 8, wherein the metal oxides are oxides of copper.

11. The method of claim 10, wherein copper is selected from a combination of Cu(I), Cu(II).

12. The composition of claim 1, wherein a weight ratio of the depolymerized chitosan and the bicarboxylic acid compound in the composite of the water-soluble chitosan nanoparticle is from 2:1 to 2.5:1.

13. The composition of claim 1, wherein the water-soluble chitosan nanoparticle is a hydrothermally-treated water-soluble chitosan nanoparticle, wherein the water-soluble chitosan nanoparticle has a diameter of about 10 nm to about 100 nm.

14. The composition of claim 13, wherein the water-soluble chitosan nanoparticle has a diameter of about 30 nm to about 50 nm.

15. The composition of claim 1, wherein the depolymerized chitosan of the water-soluble chitosan nanoparticle is defined by a cleavage at a glycoside linkage of a chitosan precursor, the cleavage at the glycoside linkage being confirmed by a Fourier Transform Infrared Spectrum.

16. The composition of claim 3, wherein the metal oxide comprises a metal oxide nanoparticle.

17. The method of claim 8, wherein the mixing comprises mixing the chitosan polymer and the bicarboxylic acid compound in a weight proportion of about 0.8:1.2 to about 1.2:0.8.

18. The method of claim 17, wherein the mixing further comprises mixing the chitosan polymer and the bicarboxylic acid compound in a weight proportion of about 1:1.

19. The method of claim 8, wherein the pressure of the hydrothermal treatment is about 2.5 atm.

\* \* \* \* \*

UNITED STATES PATENT AND TRADEMARK OFFICE
CERTIFICATE OF CORRECTION

PATENT NO. : 10,927,192 B2
APPLICATION NO. : 14/709674
DATED : February 23, 2021
INVENTOR(S) : Santra Swadeshmukul and Srijita Basumallick It is certified that error appears in the above-identified patent and that said Letters Patent is hereby corrected as shown below:

On the Title Page

(72) Inventors section; Column 1, Line 1 please delete "Basumallick Srijita" and insert with --Srijita Basumallick--

Signed and Sealed this
First Day of June, 2021

Drew Hirshfeld
*Performing the Functions and Duties of the*
*Under Secretary of Commerce for Intellectual Property and*
*Director of the United States Patent and Trademark Office*